(12) United States Patent
Nagahara et al.

(10) Patent No.: US 9,011,926 B2
(45) Date of Patent: Apr. 21, 2015

(54) METHOD FOR PRODUCING GRANULES

(71) Applicant: Takeda Pharmaceutical Company Limited, Osaka-shi, Osaka (JP)

(72) Inventors: Naoki Nagahara, Osaka (JP); Naoki Asakawa, Hikari (JP); Muneo Nonomura, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 14/488,823

(22) Filed: Sep. 17, 2014

(65) Prior Publication Data

US 2015/0072015 A1   Mar. 12, 2015

Related U.S. Application Data

(62) Division of application No. 11/884,498, filed as application No. PCT/JP2006/303455 on Feb. 24, 2006, now Pat. No. 8,871,273.

(30) Foreign Application Priority Data

Feb. 25, 2005   (JP) ................................. 2005-051732

(51) Int. Cl.
*A61K 9/16* (2006.01)
*B05D 7/00* (2006.01)
*A61K 31/4439* (2006.01)

(52) U.S. Cl.
CPC ............ *A61K 9/1682* (2013.01); *A61K 31/4439* (2013.01); *A61K 9/167* (2013.01)

(58) Field of Classification Search
None
See application file for complete search history.

(56) References Cited

U.S. PATENT DOCUMENTS

| | | | |
|---|---|---|---|
| 4,045,563 | A | 8/1977 | Berntsson et al. |
| 4,132,753 | A | 1/1979 | Blichare et al. |
| 4,628,098 | A | 12/1986 | Nohara et al. |
| 5,389,380 | A | 2/1995 | Noda et al. |
| 5,569,467 | A | 10/1996 | Ruiz |
| 5,690,960 | A | 11/1997 | Bengtsson et al. |
| 5,855,914 | A * | 1/1999 | Koyama et al. ............. 424/494 |
| 5,922,404 | A | 7/1999 | Prasad et al. |
| 6,623,759 | B2 | 9/2003 | Heese et al. |
| 6,649,186 | B1 | 11/2003 | Robinson et al. |
| 6,660,303 | B2 | 12/2003 | Staniforth |
| 2002/0054913 | A1 | 5/2002 | Heese et al. |
| 2002/0192293 | A1 | 12/2002 | Gadiraju et al. |
| 2003/0171591 | A1 | 9/2003 | Hashimoto et al. |
| 2004/0039027 | A1 | 2/2004 | Kamiyama et al. |
| 2004/0213847 | A1 | 10/2004 | Matharu et al. |
| 2004/0248941 | A1 | 12/2004 | Kamiyama et al. |
| 2005/0112193 | A1 | 5/2005 | Phillips et al. |
| 2005/0222210 | A1 | 10/2005 | Kamiyama et al. |
| 2008/0279951 | A1 | 11/2008 | Gandhi et al. |

FOREIGN PATENT DOCUMENTS

| | | | |
|---|---|---|---|
| EP | 0 005 129 | 10/1979 | |
| EP | 0 174 726 | 3/1986 | |
| EP | 0 277 741 | 8/1988 | |
| EP | 0 553 392 | 8/1993 | |
| EP | 0 958 813 | 3/1998 | |
| EP | 0 958 813 | 11/1999 | |
| EP | 1 413 294 | 4/2004 | |
| EP | 1 459 737 | 9/2004 | |
| EP | 1 584 243 | 10/2005 | |
| EP | 1 721 604 | 11/2006 | |
| JP | 3-20215 | 1/1991 | |
| JP | 4-300821 | 10/1992 | |
| JP | 5-92918 | 4/1993 | |
| JP | 63-301816 | 12/1998 | |
| JP | 11-71267 | 3/1999 | |
| JP | WO 2004/035020 | * 4/2004 | ............... A61K 9/00 |
| JP | 2004-196829 | 7/2004 | |
| WO | WO 98/10756 | 3/1998 | |
| WO | WO 98/21201 | 5/1998 | |
| WO | WO 00/78745 | 12/2000 | |
| WO | WO 2004/035020 | 4/2004 | |
| WO | WO 2004/052607 | 6/2004 | |
| WO | WO 2005/013939 | 2/2005 | |
| WO | WO 2005/039538 | 5/2005 | |

OTHER PUBLICATIONS

Wikipedia reference for mesh (scale); downloaded Dec. 5, 2014; 3-pp.*
Werner, Detlef; "Pharmaceutical Technology: Sugar spheres: A versatile excipient for oral pellet medications with modified release kinetics." published onine Apr. 1, 2006; downloaded Dec. 5, 2014; 8-pp.*
Freund products page for CF-Granulators; 1-pg; downloaded Dec. 5, 2014.*
Handbook of Pharmaceutical Excipients, Oct. 13, 1998, pp. 134-137; Hydroxyproply Cellulose.
Kojima et al., Chem Pharm Bull, 50 (12), pp. 1621-1624 (2002).
Kawashima et al., Pharm Res., vol. 10, No. 3, pp. 351-355 (1993).
Manual translation of Kashiwabara et al., JP 2003-20215 (1991).
Manual translation of Suzuki, JP 2004-300821 (1992).

* cited by examiner

*Primary Examiner* — Jeffrey T Palenik
(74) *Attorney, Agent, or Firm* — Hamre, Schumann, Mueller & Larson, P.C.

(57) ABSTRACT

In a production process of granules containing a biologically active substance, variation in the elution profile of the biologically active substance is reduced by heating the temperature of granules to about 50° C. or higher and maintaining the temperature for about 1 minute or longer. By setting the spray speed to about 90 mg/min or more per 1 g of cores when a spray agent for a primary agent containing the biologically active substance is sprayed while spraying a binding liquid to the cores and setting the total feeding weight per unit area for a centrifugal fluidized bed coating granulation machine to about 1.5 g/cm² or more, the variation in the elution profile of the biologically active substance from the granules is reduced.

5 Claims, No Drawings

METHOD FOR PRODUCING GRANULES

This application is a Division of application Ser. No. 11/884,498, filed Aug. 16, 2007, which is a U.S. National Stage application of International No. PCT/JP2006/303455, filed Feb. 24, 2006, which applications are incorporated herein by reference.

TECHNICAL FIELD

The present invention relates to a method for producing granules with reduced variation in the dissolution profile of a biologically active substance, and the like in the pharmaceutical field.

BACKGROUND ART

Among pharmaceutical preparations, orally-administered preparations are the most frequently used dosage forms. In recent years, in the light of improvement of QOL, many orally-administered preparations whose beneficial effects can be sustained by one or two doses a day have been developed. Although there are some preparations capable of sustaining their beneficial effects by one or two doses a day due to the properties of biologically active substances themselves contained in the preparations, many attempts to prolong the beneficial effects of pharmaceutical preparations by devising in production of the preparations has been made. For orally-administered sustained-release preparations, various systems including controlled release induced by controlling the diffusion of a biologically active substance using a controlled-release film or matrix, controlled release of a biologically active substance induced by erosion of a base material, controlled release of a pH-dependent biologically active substance, and time-limited controlled release for releasing a biologically active substance after a given lag time have been developed and applied. Since such an orally-administered sustained-release preparations moves through the digestive tract while it releases a biologically active substance after being administered, variation in the speed moving through the digestive tract influences production of the beneficial effect of the preparation, and the influence is different depending on the dosage form of the preparation. It has been known that a granule or fine granule that is used in multiple units is generally less influenced by the moving speed through the digestive tract than a tablet that is used in a single unit.

Since a conventional granule or fine granule preparation containing a biologically active substance often had variation in the dissolution profile (variation of dissolution) between preparations or lots, it was difficult to stably obtain a granule or fine granule preparation having a desirable dissolution profile required for producing a desirable effect. Therefore, in order to suppress variation in the dissolution profile, a granule or fine granule preparation was forced to be produced under a very narrow range of production conditions.

Various methods for producing granules are known. As one of them, Patent Document 1 discloses a method for producing a dry-coated powder having substantially a particle diameter of 500 μm or less and having a controlled dissolution property wherein a fine granular core is coated with at least one biologically active substance in combination with a water-soluble polymer.

The present inventors studied methods for producing granules having a stable dissolution profile, and as a result, found that the present invention can remarkably reduce variation in dissolution profiles between preparations or lots to provide granules stably having a desired dissolution profile. Finally the present invention was completed. That is, the present invention relates to a method for improving variation in the dissolution of a biologically active substance from granules containing the biologically active substance, which comprises heating the temperature of the granules to about 50° C. or higher and then maintaining the granules at the said temperature for about 1 minute or longer in a process for producing the granules. The present invention also relates to a method for producing granules containing a biologically active substance wherein the above-mentioned improving method is utilized.

The phrase "improving variation in the dissolution" as used herein means reducing variation in the dissolution profile (change in the dissolution rate of a biologically active substance from a pharmaceutical preparation with time). The phrase "maintaining the granules at the said temperature for about 1 minute or longer" as used herein means that the total time for maintaining the granules at the said temperature is 1 minute or longer, and continuous maintenance for 1 minute or longer and intermittent maintenance for a total time of 1 minute or longer are included. The dissolution rate means a proportion (percentage) of the dissolved amount of a biologically active substance to the amount (content) of the biologically active substance contained in a pharmaceutical preparation.

Patent Document 1: JP-A 5-92918

DISCLOSURE OF THE INVENTION

Problems to be Solved by the Invention

An object of the present invention is to improve variation in the dissolution profile of an active pharmaceutical ingredient from granules containing a biologically active substance.

Means for Solving the Problem

The present invention provides:
[1] a method for producing granules containing a biologically active substance, which comprises, in a process for producing the granules, heating the temperature of the granules to about 50° C. or higher and then maintaining the granules at the said temperature for about 1 minute or longer;
[2] the method according to the above [1], which is a method for producing coated granules;
[3] the method according to the above [1], wherein the temperature of the granules is heated to about 60° C. or higher;
[4] the method according to the above [1], wherein the temperature of the granules is heated to about 65° C. or higher;
[5] the method according to the above [1], wherein the granules are maintained at the said temperature for about 3 minutes or longer;
[6] a centrifugal fluidized bed granulation method for granules of an active pharmaceutical ingredient, which comprises spraying or dusting a spraying or dusting material containing an active pharmaceutical ingredient containing a biologically active substance at a spraying or dusting speed of about 90 mg/min or more per 1 g of cores while spraying a binder liquid to the cores, wherein a total feeding weight (i.e. a sum of the weight of the cores and the weight of the spraying or dusting material containing an active pharmaceutical ingredient) per unit area for a centrifugal fluidized bed coating granulation machine is about 1.5 g/cm² or more;
[7] the method according to the above [6], wherein the spraying or dusting speed of the spraying or dusting material containing an active pharmaceutical ingredient is from about 90 to about 250 mg/min;

[8] the method according to the above [6], wherein the ratio of (spraying or dusting speed of the spraying or dusting material containing an active pharmaceutical ingredient per 1 g of cores)/(linear velocity) is from 0.27 to 2;
[9] the method according to the above [6], wherein the total feeding weight per unit area for a centrifugal fluidized bed coating granulation machine is from about 1.5 to about 6 g/cm$^2$; and
[10] a granule obtained by the method according to the above [1] or by the granulation method according to the above [6].

Effect of the Invention

According to the method for improving variation in the dissolution of a biologically active substance of the present invention, in a process for producing granules containing a biologically active substance, simply heating the temperature of granules to a predetermined temperature and then maintaining the granules at the said temperature for a predetermined time can lead to reduced variation in the dissolution profile of the biologically active substance, and thereby a design of a pharmaceutical preparation capable of stably maintaining an effective blood concentration of a drug is facilitated. Therefore, according to the present invention, it is possible to produce granules having a stable dissolution profile without a very narrow range of production conditions, to easily scale up the production for industrial-scale implementation, and to ensure consistent quality of the granules produced.

BEST MODE FOR CARRYING OUT THE INVENTION

The biologically active substance used in the present invention may be a drug having low toxicity. The biologically active substance is mixed and granulated with a pharmacologically acceptable carrier according to a per se known method to produce granules. The obtained granules can be safely orally administered directly as a granular preparation or after they are formulated into a capsule, a tablet, an orally disintegrating tablet, a sustained release preparation or the like.

The term "granules" as used herein refers to granules having an average particle diameter of 50 µm to 5 mm, preferably 100 µm to 3 mm, and more preferably 100 µm to 2 mm. Fine granules prescribed in "Minimum Requirement for Antibiotic products of Japan, 1993" (a preparation of granules of which 95% or more can pass through a 500 µm mesh sieve) are also included in the above-mentioned "granules".

Since an object of the present invention is to improve variation in the dissolution profile of an active pharmaceutical ingredient from granules containing a biologically active substance, the present invention can be used for producing granules that need such improvement. Therefore, the biologically active substance used in the present invention may be a biologically active substance having variation in the dissolution profile between productions or lots required to be controlled. Examples of the biologically active substance include, but not limited to, central nervous system drugs, circulatory system drugs, respiratory system drugs, digestive system drugs, antibiotics, metabolic system drugs, vitamins and antacids. Several kinds (two or three kinds) of the biologically active substances may be used.

Other examples of the biologically active substance include imidazole compounds or salts thereof such as lansoprazole or an optically active form thereof as described later, particularly benzimidazole compounds, and proton pump inhibitors (PPI) such as imidazole derivatives or salts thereof, or optically active forms thereof.

Examples of the pharmacologically acceptable carrier that may be used for the production of granules of the present invention include various organic or inorganic carriers conventionally used as pharmaceutical materials, and specific examples thereof include excipients, lubricants, binders, disintegrants, water soluble polymers and basic inorganic salts for solid preparations. In addition, conventional additives such as antiseptics, antioxidants, colorants, sweeteners, acidulants, foaming agents and flavors may be optionally used.

Examples of the excipient include lactose, white sugar, D-mannitol, starch, corn starch, crystalline cellulose, light silicic acid anhydride and titanium oxide.

Examples of the lubricant include magnesium stearate, sucrose fatty acid ester, polyethyleneglycol, talc and stearic acid.

Examples of the binder include hydroxypropyl cellulose, hydroxypropylmethyl cellulose, crystalline cellulose, starch, polyvinyl pyrrolidone, gum Arabic powder, gelatin, pullulan and low-substituted hydroxypropyl cellulose.

Examples of the disintegrant include (1) crospovidone, (2) disintegrants called as super-disintegrants such as croscarmellose sodium (manufactured by FMC-Asahi Kasei Co,) and carmellose calcium (manufactured by Gotoku Chemical Company Ltd.), (3) carboxymethyl starch sodium (for example, manufactured by Matsutani Chemical Industry Co. Ltd.), (4) low-substituted hydroxypropyl cellulose (for example, manufactured by Sin-Etsu Chemical. Co. Ltd.) and (5) corn starch. The "crospovidone" may be any cross-linked polymers having the chemical name 1-ethenyl-2-pyrrolidinone homopolymer including polyvinyl pyrrolidone (PVPP) and 1-vinyl-2-pyrrolidinone homopolymer, and specific examples thereof include KOLIDON CL (trade name; manufactured by UASF Co.), POLYPLASDONE XL (trade name; manufactured by ISP Co.), POLYPLASDONE XL-10 (trade name; manufactured by ISP Co.) and POLYPLASDONE INF-10 (trade name; manufactured by ISP Co.).

Examples of the "water-soluble polymer" include ethanol-soluble water-soluble polymers [for example, cellulose derivatives such as hydroxypropyl cellulose (hereinafter abbreviated as HPC, in some cases) and polyvinyl pyrrolidone], and ethanol-insoluble water-soluble polymers [for example, cellulose derivatives such as hydroxypropylmethyl cellulose (hereinafter abbreviated as HPMC, in some cases)], methyl cellulose and sodium carboxymethyl cellulose, sodium polyacrylate, polyvinyl alcohol, sodium alginate and guar gum.

Examples of the "basic inorganic salt" include basic inorganic salts of sodium, potassium, magnesium and/or calcium, preferably basic inorganic salts of magnesium and/or calcium, and more preferably basic inorganic salts of magnesium. Examples of the basic inorganic salt of sodium include sodium carbonate, sodium hydrogen carbonate and disodium hydrogen phosphate. Examples of the basic inorganic salt of potassium include potassium carbonate and potassium hydrogen carbonate. Examples of the basic inorganic slat of magnesium include heavy magnesium carbonate, magnesium carbonate, magnesium oxide, magnesium hydroxide, magnesium metasilicate aluminate, magnesium silicate, magnesium aluminate, synthetic hydrotalcite [$MgAl_2(OH)_{16}.CO_3.4H_2O$] and aluminum/magnesium hydroxide, preferably heavy magnesium carbonate, magnesium carbonate, magnesium oxide and magnesium hydroxide. Examples of the basic inorganic salt of calcium include precipitated calcium carbonate and calcium hydroxide.

Examples of the "antiseptic" include parahydroxybenzoic acid esters, chlorobutanol, benzyl alcohol, phenethyl alcohol, dehydroacetic acid and sorbic acid.

Examples of the "anti-oxidant" include sulfite, ascorbic acid and α-tocopherol.

Examples of the "colorant" include edible dyes such as edible yellow No. 5, edible red No. 2 and edible blue No. 2; edible lake pigments and ferric oxide.

Examples of the "sweetener" include saccharin sodium, dipotassium glycyrrhizinate, aspartame, stevia and thaumatin.

Examples of the "acidulant" include citric acid (citric anhydride), tartaric acid and malic acid.

Examples of the "foaming agent" include sodium bicarbonate.

The "flavor" may be synthetic or natural, and examples thereof include lemon, lime, orange, menthol and strawberry flavors.

The content of the excipient in the granule is not particularly limited and it is, for example, from about 20 to about 99.9% by weight, preferably from about 40 to about 95% by weight.

The content of the lubricant in the granule is not particularly limited and it is, for example, from about 0.01 to about 3% by weight, preferably from about 0.05 to about 2% by weight.

The content of the binder in the granule is, for example, from about 0.1 to about 10% by weight, preferably from about 1 to about 5% by weight.

The content of the disintegrant in the granule is, for example, from about 0.1 to about 30% by weight, preferably from about 3 to about 25% by weight.

The content of the water-soluble polymer in the granule is, for example, from 0.1 to about 50% by weight, preferably from 1 to about 30% by weight.

The content of the basic inorganic salt in the granule is, for example, from 0.1 to 30% by weight, preferably from 1 to 20% by weight.

The contents of the antiseptic, anti-oxidant, colorant, sweetener, acidulant, foaming agent and flavor in the granule are optionally determined and for example, they are each from about 0.0001 to about 3% by weight.

The granules produced by the method of the present invention can be formulated into orally-administered preparations according to a per se known method, for example, by adding the above-mentioned carriers such as excipient, disintegrant, binder and lubricant to the biologically active substance, granulating the mixture by compression molding or the like, and then optionally coating the obtained granules by a per se known method for the purpose of taste masking, enteric coating or sustained release. When the granules are formulated into enteric coated preparations, an intermediate layer may be provided between an enteric layer and a drug-containing layer for the purpose of separation of the both layers by a per se known method.

The production method of the present invention is characterized by, in a process for producing granules containing a biologically active substance, heating the temperature of the granules to about 50° C. or higher and then maintaining the granules at the said temperature for about 1 minute or longer. The phrase "maintaining the granules at the said temperature for about 1 minute or longer" means that the total time for maintaining the granules at the said temperature is 1 minute or longer (preferably 3 minutes or longer), and continuous maintenance for 1 minute or longer (preferably for 3 minutes or longer) and intermittent maintenance for 1 minute or longer (preferably for 3 minutes or longer) in total are included.

The "said temperature" as used herein means the temperature of the heated granules. In the present invention, the said temperature is 50° C. or higher, preferably 60° C. or higher and more preferably 65° C. or higher, and the upper limit of the said temperature is selected within a temperature range in which the stability of the drug is not impaired.

The "temperature of granules" does not mean a setting temperature of a system which is controlled by a granule producing apparatus or a temperature control device, such as air supply temperature ox exhaust temperature, but means the granule's own temperature, a so-called "product temperature".

The timing for heating is not particularly limited, and heating may be performed at any time of
(1) during a step of adding and mixing the biologically active substance and the above-mentioned carrier,
(2) during a granulation step, or
(3) after a granulation step.

In particular, heating is preferably performed after a granulation step.

The desirable heating temperature is from about 50° C. to abut 80° C., more preferably from about 65° C. to about 75° C.

After heating, the desirable time for maintaining the granules at the said temperature is not particularly limited as long as the time is about 1 minute or longer (preferably 3 minutes or longer) and the stability of an active pharmaceutical ingredient is not affected, and it is from about 1 minute to about 6 hours, preferably from about 1 minute to about 3 hours, more preferably from about 1 minute to about 1 hour, and particularly preferably from abut 3 minutes to about 30 minutes.

The term "maintaining" as used herein means that the granules may be maintained within the above-mentioned prescribed temperature range, that is, about 50° C. or higher, preferably from about 50° C. to about 80° C. and more preferably from about 65° C. to about 75° C., for a prescribed time, and in addition to the maintenance at a constant temperature, the temperature may be elevated or lowered within the above-mentioned prescribed temperature range. The term "maintaining" also means that the total time for maintaining the granules within the above-mentioned prescribed temperature range, and that the granules may be continuously maintained for a desired time or longer or the total time for intermittent maintenance within the prescribed temperature range may be a desired time or longer.

The temperature to be heated and the time for maintenance at the temperature is selected within the range in which the stability of the drug is not impaired even by heating the granules to a prescribed temperature and maintaining the granules at the said temperature for a given period of time.

The granulation method is not particularly limited, and the granules can be produced by a per se known method, for example, a dry granulation method, a wet granulation method such as extrusion granulation or tumbling granulation, a spray method or the like.

The dry granulation method comprises steps of strongly compressing raw material powder directly or after mixing with the above-mentioned appropriate binder and the like to obtain small masses, and appropriately crushing and granulating them.

The wet granulation method comprises steps of adding a solution or suspension of the above-mentioned appropriate binder to raw material powder and mixing them followed by granulation, drying and grading. Alternatively, dense spherical particles may be formed by tumbling wetted raw material powder with vibration or rotational motion.

The spray method comprises steps of spraying slurry of raw materials as minute droplets using a nozzle or rotating disk, and drying the droplets by blowing hot air.

Preferable granules to which the production method of the present invention is applicable are coated granules.

The term "coated" as used herein not only means that the entire surface of a core granule (including a fine granular core; hereinafter the "core granule" may be referred to as a "core grain") which is a subject for coating is coated, but also means that the surface of a core granule is partially coated or a coating agent is adsorbed or absorbed to the surface of a core granule.

The core granule may contain a biologically active substance as an active pharmaceutical ingredient. Alternatively, the core may not contain a biologically active substance because release of the drug can be controlled by allowing a coating layer to contain the active pharmaceutical ingredient.

The core granule is preferably spherical for the purpose of reducing variation of coating as well as increasing the amount of coating.

The term "spherical" as used herein means a shape having a curved surface including a shape having ellipsoidal cross sections, an eggplant shape and a droplet shape as well as a perfectly spherical shape.

The particle diameter of the core granule may be substantially 5000 μm or less, and for example, it is approximately from 50 to 5000 μm, preferably from 100 to 3000 μm, and more preferably from 200 to 2000 μm.

An example of the core granule having the above-mentioned particle diameter includes a granule (a granule of an active pharmaceutical ingredient) obtained by mixing the above-mentioned biologically active substance and the above-mentioned pharmacologically acceptable carrier, and then granulating the mixture.

A coating agent used for coating is not particularly limited, and for example, it is prepared by mixing and dispersing one or more substances selected from hydrophobic substances, plastic excipients and enteric polymer substances into a lower alcohol such as ethanol, water or a mixed solvent thereof. A coating liquid of ethyl cellulose, an ethyl acrylate-methyl methacrylate copolymer, a methacrylic copolymer, hydroxypropylmethyl cellulose phthalate or the like may be also used.

Examples of the hydrophobic substance include ethyl cellulose, ethyl acrylate-methyl methacrylate copolymers, aminoalkyl methacrylate copolymers and carboxyvinyl polymers.

Examples of the plasticizing excipient include triethyl citrate, glycerin fatty acid esters, cetanol, hardened caster oil, hardened rape oil and carnauba wax.

Examples of the enteric polymer substance include methacrylate copolymers, hydroxypropylmethyl cellulose phthalate, hydroxypropyl cellulose acetate, hydroxypropylmethyl cellulose acetate succinate, carboxymethylethyl cellulose and acetic acid phthalic acid cellulose.

The coating can be performed by a conventional coating method, and for example, spray coating may be performed by a fluidized bed coating method or the like. In addition, the coated solid thus obtained may be compression molded to produce the granule of the present invention.

In producing the coated granule, an inert carrier such as NONPAREIL [NONPAREIL-101, (particle diameter 850-710, 710-500, 500-355 μm), NONPAREIL-103 (particle diameter 850-710, 710-500, 500-355 μm) or NONPAREIL-105 (particle diameter 710-500, 500-355, 300-180 μm), manufactured by Freund Co.] or CELPHERE [CP-507 (particle diameter 500-710 μm) and CP-305 (particle diameter 300-500 μm), manufactured by Asahi Kasei Co.] may be used as a core.

Cores of the inert carrier can be sprayed with a mixed liquid containing a water-soluble polymer and a biologically active substance to obtain coated granules (granules of an active pharmaceutical ingredient).

The mixed liquid may be a solution or dispersion. The mixed liquid can be prepared using water, an organic solvent such as ethanol, or a mixture thereof.

Examples of the water-soluble polymer include ethanol-soluble water-soluble polymers such as hydroxypropyl cellulose (hereinafter abbreviated as HPC, in some cases) and polyvinyl pyrrolidone; and ethanol-insoluble water-soluble polymers such as hydroxypropylmethyl cellulose (hereinafter abbreviated as HPMC, in some cases), methyl cellulose, carboxymethyl cellulose sodium, sodium polyacrylate, polyvinyl alcohol, sodium alginate and guar gum. The dissolution property of the drug can be controlled by using the ethanol-soluble water-soluble polymer in combination with the ethanol-insoluble water-soluble polymer, or using the water-soluble polymers having different viscosity together.

The concentration of the water-soluble polymer in the mixed liquid varies depending on the proportions of the drug and additives to be used, and it is usually from about 0.1 to about 50% by weight, preferably from about 0.5 to about 10% by weight.

The coating layer containing the drug may contain an additive such as low substituted hydroxypropyl cellulose (hereinafter abbreviated as L-HPC, in some cases) or the like to enhance the strength of the granule.

Examples of the additive include excipients such as lactose, corn starch, sucrose, talc, crystalline cellulose, mannitol, colloidal silicon dioxide, magnesium carbonate, calcium carbonate and L-cysteine; binders such as pregelatinized starch, partial pregelatinized starch, methyl cellulose, carboxymethyl cellulose, polyvinyl pyrrolidone, pullulan, dextrin and gum Arabic; disintegrants such as carboxymethyl cellulose calcium, starch, cross-linked carboxymethyl cellulose sodium and cross-linked insoluble polyvinyl pyrrolidone; and colorants such as titanium oxide, ferric oxide and tar dye. Two or more kinds of these additives may be used in combination.

The content of the water-soluble polymer such as HPC and/or HPMC in the coating layer may be within a range of contents in which the water-soluble polymer can control the dissolution property of the drug from the granule, and for example, it is from about 0.1% by weight to about 50% by weight, preferably from about 1% by weight to about 30% by weight.

The dissolution property of the drug can be controlled by selecting the grade of viscosity and the content of the water-soluble polymer such as HPC and/or HPMC, and the ratio between the ethanol-soluble water-soluble polymer (for example HPC) and the ethanol-insoluble water-soluble polymer (for example HPMC). The dissolution property of the drug can be suitably controlled with being little affected by a liquid for dissolving the drug.

The proportion of the coating layer to the core granule can be selected within a range of proportions in which the dissolution property of the biologically active substance can be controlled, and for example, it is about 5 to 400 parts by weight per 100 parts by weight of the core. However, the proportion is not limited thereto.

The coating layer may consist of plural layers, and at least one layer of the plural coating layers may contain the biologically active substance.

In this case, the blending ratio or the grade of viscosity of the water-soluble polymer may be selected for forming each coating layer, or the content of the biologically active substance in each coating layer may be changed sequentially or stepwise by sequential coating with mixed liquids containing different proportions of the biologically active substance or other additives. In addition, an inert, coating film (intermediate coating layer) may be formed between respective layers by a known method to block the respective layers containing the biologically active substance.

When a plurality of biologically active substances having poor compatibility are blended, respective mixed liquids may be used simultaneously or separately to coat the core.

Another method for producing the coated granule (the granule of the active pharmaceutical ingredient) may comprise spraying or dusting a spraying or dusting material prepared by mixing the biologically active substance and/or additives while spraying a solution or a dispersion containing the water-soluble polymer onto the core (for example the above-mentioned inert carrier).

When the biologically active substance is incorporated into the spraying or dusting material, the solution or dispersion containing the water-soluble polymer may or may not contain the biologically active substance. Using this method, the coating layer can be formed by a simple operation of merely spraying or dusting the spraying or dusting material.

The average particle diameter of the spraying or dusting material is usually about 100 μm or less, preferably about 50 μm or less.

Coated granules obtained by spraying or dusting the spraying or dusting material may be further coated with one or more layers. The coated granules obtained by spraying or dusting the spraying or dusting material contain the biologically active substance, and if the coated granules are further coated, additional layers may also contain the biologically active substance.

In addition, an inert coating film (intermediate coating layer) may be formed between respective layers by a known method to block the respective layers containing the drug.

Granulation is performed by coating the core with the mixed liquid or the spraying or dusting material by the above-mentioned method. The granulation temperature is within a temperature range in which the stability of the biologically active substance is not impaired.

When the stability of the biologically active substance is high, the temperature of the mixed liquid or the spraying or dusting material usually does not need to be particularly adjusted and the granulation can be usually performed at a room temperature of 1 to 30° C.

A method for coating the core is not particularly limited, and for example, a conventional apparatus such as a centrifugal tumbling coating granulation machine (hereinafter referred to as a centrifugal tumbling granulation machine, in some cases), a centrifugal fluidized bed coating granulation machine (hereinafter referred to as a CF machine, in some cases), a fluidized bed coating granulation machine, a tumbling fluidized bed coating machine (hereinafter referred to as a composite fluidized bed coating machine, in some cases) or a stirring granulation machine can be used.

The granules are preferably produced by a centrifugal fluidized bed granulation method using a centrifugal fluidized bed coating granulation machine.

An example of the centrifugal fluidized bed coating granulation machine includes, but not limited to, a CF granulator manufactured by Freund Co.

An example of the centrifugal tumbling coating granulation machine includes, but not limited to, GRANULEX manufactured by Freund Co.

An example of the fluidized bed coating granulation machine includes, but not limited to, FLOW COATER manufactured by Freund Co.

Examples of the tumbling fluidized bed coating machine include, but not limited to, SPIRAL FLOW manufactured by Freund Co. and MULTIPLEX manufactured by POWREX Co.

The present invention is based on the finding that variation in the release profile of a drug can be reduced by heating the temperature of a granule to a predetermined temperature and then maintaining the granule at the said temperature for a given period of time in a process for producing the granule. Particularly in the case where a core granule is coated with a spraying or dusting material by a centrifugal fluidized bed granulation method on an industrial scale, the objective of the present invention of reducing variation in the release profile of a drug from granules can be also attained by controlling the feeding weight (i.e. a sum of the weight of cores and the weight of a spraying or dusting material containing an active pharmaceutical ingredient), the spraying or dusting speed of a spraying or dusting material or the rotational speed of a rotor during centrifugal fluidized bed coating granulation.

That is, the present invention also provides:
(1) a centrifugal fluidized bed granulation method for granules of an active pharmaceutical ingredient, which comprises spraying or dusting a spraying or dusting material containing an active pharmaceutical ingredient containing a biologically active substance at a spraying or dusting speed of about 90 mg/min or more per 1 g of cores while spraying a binder liquid to the cores;
(2) the method according to the above (1), wherein the spraying or dusting speed of the spraying or dusting material containing an active pharmaceutical ingredient is from about 90 to about 250 mg/min;
(3) the method according to the above (1), wherein the spraying or dusting material containing an active pharmaceutical ingredient is sprayed or dusted in an amount twice or more the weight of the cores;
(4) the method according to the above (1), wherein the spraying or dusting material containing an active pharmaceutical ingredient is a mixture of a biologically active substance, a basic inorganic salt, a binder, a disintegrant and an excipient;
(5) the method according to the above (i), wherein the core is a spherical granule of lactose and/or crystalline cellulose;
(6) a centrifugal fluidized bed granulation method for granules of an active pharmaceutical ingredient, wherein a total feeding weight per unit area for a centrifugal fluidized bed coating granulation machine is about 6 $g/cm^2$ or less (preferably about 1.5 to about 6 $g/cm^2$);
(7) the method according to the above (1), wherein the total feeding weight per unit area for a centrifugal fluidized bed coating granulation machine is about 6 $g/cm^2$ or less; and
(8) the method according to the above (1), wherein the ratio of (spraying or dusting speed of the active pharmaceutical ingredient per 1 g of cores)/linear velocity is from 0.27 to 2.

The centrifugal fluidized bed granulation method generally comprises allowing spherical granules or cores to perform planetary motions with centrifugal force produced by rotation of a rotor and slit air, and spraying water or a solution containing a binder liquid onto the surfaces of the spherical granules or cores, while coating the surfaces of the spherical granules or cores with a spraying or dusting material containing an active pharmaceutical ingredient. According to the centrifugal fluidized bed granulation method, spherical granules having high sphericity and narrow particle diameter distribution can be obtained.

Examples of the "core" to be used include granules obtained by mixing and granulating the above-mentioned biologically active substance and the above-mentioned pharmacologically acceptable carrier, and the above-mentioned inert carrier. The inert carrier is preferably used as the core when the biologically active substance is contained in the spray.

Examples of the "binder liquid" include a solution and a dispersion containing the above-mentioned water-soluble polymer.

Examples of the "spraying or dusting material containing an active pharmaceutical ingredient" include a powdery biologically active substance as it is, and the above-mentioned powder spray prepared by mixing a biologically active substance and/or additives.

Spraying or dusting of the spraying or dusting material containing an active pharmaceutical ingredient is usually controlled by the spraying or dusting weight per minute depending on the kind of a spraying or dusting machine, and it is sprayed or dusted at about 90 mg/min or more, preferably from about 90 to about 250 mg/min, more preferably from about 100 to about 200 mg/min, and particularly from about 120 to about 160 mg/min per 1 g of cores. The spraying or dusting speed is preferably about 1.5 to about 5 times higher than the sprayor dusting speed used for producing conventional coated granules.

Although spraying or dusting may be started at the above-mentioned speed, usually, the spraying or dusting speed may be gradually increased from a low speed to the above-mentioned speed. The spraying or dusting speed may be slightly increased or decreased during the spray step.

Raw materials are fed to a rotor part of the centrifugal fluidized bed coating granulation machine, and the total feeding weight of the raw materials per unit area for the machine is about 6 $g/cm^2$ or less (preferably from about 1.5 to about 6 $g/cm^2$), more preferably from about 2 to about 4 $g/cm^2$. The "total feeding weight" means the total weight of all raw materials for producing the granule, for example a sum of the weight of the cores and the weight of the spraying or dusting material containing an active pharmaceutical ingredient.

Since shear stress is low during granulation and therefore variation in the drug release profile does not occur when the total feeding weight is small in the centrifugal fluidized bed granulation method, that is, when a small size centrifugal fluidized bed coating granulation machine (the total feeding weight per unit area is less than about 1.5 $g/cm^2$) is used, the present invention is applied to the centrifugal fluidized bed granulation method using a middle or larger size centrifugal fluidized bed coating granulation machine (the total feeding weight per unit is about 1.5 $g/cm^2$ or more).

The spraying or dusting material containing an active pharmaceutical ingredient is sprayed or dusted in an amount of 0.1 times or more, preferably 0.5 to 5 times, more preferably from 1 to 4 times the weight of the cores.

For the centrifugal fluidized bed granulation method, the cores are fed to a rotor part of a machine and then are fluidized by rotating the rotor. While a rotational speed of the rotor depends on the size of a machine, a speed at the outer circumference of the rotor (linear velocity) does not depend on the size of a machine and a preferable linear velocity is determined depending on the kind of a spraying or dusting material containing an active pharmaceutical ingredient. For example, the desired linear velocity for some spraying or dusting material containing an active pharmaceutical ingredient is 300 m/min or less, but it is not limited thereto. A preferable linear velocity is also determined depending on the spraying or dusting speed of a spraying or dusting material containing an active pharmaceutical ingredient. In other words, the spraying or dusting speed of a spraying or dusting material containing an active pharmaceutical ingredient and a linear velocity are complementary to one another, and a preferable ratio between them (spraying or dusting speed of (a spraying or dusting material containing an active pharmaceutical ingredient per 1 g of cores)/(linear velocity)) is determined. For example, the ratio of active pharmaceutical ingredient spraying or dusting speed/linear velocity is in the range from 0.27 to 2, preferably from 0.35 to 1.5, and more preferably from 0.45 to 1.

Although when a feeding weight and/or a spraying or dusting speed of the spraying or dusting are selected as described above in centrifugal fluidized bed coating granulation, the objective of the present invention of reducing variation in the release profile of a drug from a granule can be attained without using "the method comprising heating the temperature of granules to about 50° C. or more and maintaining the granules at the said temperature for about 1 minute or more" of the present invention, these methods may be combined.

The coated granules obtained as described above may be dried and then sieved to obtain dry coated granules having a uniform particle diameter. An example of the sieve to be used is a round sieve with a mesh size of 12 (1400 μm).

The drying is performed at about 40° C. by, for example, vacuum drying, but it is not limited thereto.

The granules thus obtained (granules of an active pharmaceutical ingredient, granules having intermediate coating layers, and the like) may be optionally coated by a conventional method for the purpose of taste masking, enteric coating, gastric coating or the like.

Examples of a coating agent include hydroxypropylmethyl cellulose, ethyl cellulose, hydroxymethyl cellulose, hydroxypropyl cellulose, polyoxyethylene glycol, Tween 80, Prulonic F68, cater oil, cellulose acetate phthalate, hydroxypropylmethyl cellulose phthalate (hereinafter, abbreviated as HP-55), hydroxymethyl cellulose acetate succinate, acrylate copolymers, carboxymethylethyl cellulose, polyvinyl acetal diethylamino acetate, shellac, waxes, and dyes such as talc, titanium oxide and ferric oxide.

In the case of using PPI as the biologically active substance, it is particularly desirable to coat granules with an enteric coating. Examples of the material of the desirable enteric coating layer include cellulose acetate phthalate (CAP), hydroxypropylmethyl cellulose phthalate [HP-55 and HP-50 (trade names; manufactured by Shin-Etsu Chemical Co., Ltd.)], hydroxymethyl cellulose acetate succinate [HP-MCAS (trade name; manufactured by Shin-Etsu Chemical Co., Ltd.)], methyl methacrylate-methacrylic acid copolymers [EDRAGIT L100 (methacrylic acid copolymer L) or EUDRAGIT S100 (methacrylic acid copolymer 5), trade names; manufactured by Roehm Co.], and methacrylic acid-ethyl acrylate copolymers [EUDRAGIT L30D-55 (methacrylic acid copolymer LD, trade name; manufactured by Roehm Co.), COLICOAT MAE30DP (trade name; manufactured by BASF Co.), and POLYKID PA30 (trade name; manufactured by Sanyo Chemical Industry Co.)].

In the case of applying the production method of the present invention to production of coated granules, the timing for heating is not particularly limited.

When granules obtained by mixing and granulating the biologically active substance and the pharmacologically acceptable carrier are coated as core granules, the heating may be performed at any time of:

(1) during the granulation step for granules of the active pharmaceutical ingredient;
(2) after the granulation step for granules of the active pharmaceutical ingredient and before the step of coating with an optionally formed intermediate layer;
(3) during the step for coating with an optionally formed intermediate layer or after the coating step;
(4) before various coating steps such as an enteric coating step;
(5) during the above-mentioned various coating steps; and
(6) after the above-mentioned various coating steps.

The timing for heating is preferably (2) after the granulation step for granules of the active pharmaceutical ingredient and before the step of coating with an optionally formed intermediate layer, (3) during the step for coating with an optionally formed intermediate layer or after the coating step, (4) before various coating steps such as an enteric coating step, (5) during the above-mentioned various coating steps, or (6) after the above-mentioned various coating steps.

The coating layer may consist of plural layers, as described above. In the case of coating with a plurality of layers, the timing for heating may be before, during or after the coating step of each layer.

In the case of drying the granules after the coating step, the timing for heating may be before, during or after drying.

In the case of applying the production method of the present invention to production of coated granules, the desirable temperature for heating and the desirable time for maintaining the granules at the said temperature after heating are the same as described above.

More preferable coated granules to which the production method of the present invention is applicable are granules with controlled release of the biologically active substance.

The control of release of the biologically active substance in the "granules with controlled release of the biologically active substance" is attained by coating granules containing the biologically active substance with a film capable of controlling release of the biologically active substance, or dispersing the biologically active substance in a controlled release matrix. "The granules with controlled release of the biologically active substance" include granules coated with a conventional enteric coating film that dissolves at about pH 5.5.

The "controlled release coating film" as used herein refers to a film having a function of delaying or sustaining release of the biologically active substance for a longer time than a conventional enteric coating film that dissolves at about pH 5.5, including a pH-dependent soluble coating film that dissolves at a higher pH region or a diffusion-controlled film that does not dissolve itself and releases the biologically active substance through pores formed on the film; and does not include a conventional enteric coating film that dissolves at about pH 5.5 and releases the biologically active substance by promptly dissolving in the intestinal juice. The pH as used herein refers to pH adjusted with a McIlvaine solution or Clark-Lubs solution. Hereinafter, the pH of a film that dissolves pH-dependently refers to the above-mentioned pH.

The coating film of the "controlled release coating film" includes a coating layer having a larger thickness as well as a coating layer in a film form, and further, a coating layer that covers almost all portions of the inner core granules or layers although partially uncovered portions remain as well as a coating layer that perfectly covers the inner core granules or layers (a coating film that covers at least 80% or more, preferably all of the surface of the inner core granules or layers).

When a pharmaceutical preparation containing such granules with controlled release of the biologically active substance is orally administered, absorption of the biologically active substance through the digestive tract is controlled by any one of two systems taking advantage of (1) controlled release of the biologically active substance by means of the controlled release granules and (2) prolonged residence time of granules in the digestive tract by means of a gel-forming polymer, or a combination of these systems. When granules containing the gel-forming polymer are orally administered, the gel-forming polymer rapidly absorbs water in the digestive tract to form an adhesive gel, and then, the gel slowly moves through the digestive tract while keeping the granules on the surface or inside. During the movement, release of the biologically active substance is controlled, the biologically active substance is released from the granules continuously or pulse-wise in a controlled manner, and consequently, sustained absorption and sustained beneficial effect are attained.

The above-mentioned system that enables a therapeutically effective concentration to be sustained by controlling release for a long term has not only the advantage of reducing the number of doses, but also the advantages of effective therapy at a low dosage, alleviation of side effects caused by rising of the blood concentration, and the like.

Use of the production method for granules of the present invention enables the above-mentioned controlled release system to work without variation between preparations or lots and therefore a desired dissolution profile can be stably obtained.

The gel-forming polymer may be any polymer as long as it forms a highly viscous polymer rapidly on contact with water and prolongs the residence of the biologically active substance in the digestive tract. The preferable gel-forming polymer has a viscosity of 3,000 mPa·s or more in 5% aqueous solution at 25° C. In addition, it is usually preferable that the gel-forming polymer has a molecular weight from 400,000 to 10,000,000. The gel-forming polymer is suitably powdery, granular or fine granular for the purpose of formulation. Examples of the gel-forming polymer include polyethylene oxide [PEO, for example POLYOX WSR303 (molecular weight 7,000,000), POLYOX WSR Coagulant (molecular weight 5,000,000), POLYOX WSR 301 (molecular weight 4,000,000), POLYOX WSR N-60K (molecular weight 2,000,000), POLYOX WSR 205 (molecular weight 600,000), manufactured by Dow Chemical Co.], hydroxypropylmethyl cellulose [HPMC, METLOSE 90SH10000, METLOSE 90SH50000, METLOSE 90SH30000, manufactured by Shin-Etsu Chemical Co., Ltd.], carboxymethyl cellulose (CMC-Na, SANLOSE F-1000MC), hydroxypropyl cellulose (HPC, for example HPC—H, manufactured by Nippon Soda Co.), hydroxyethyl cellulose (HEC), carboxyvinyl polymers (HIVISWAKO (R) 103, 104, 105, manufactured by Wako Pure Chemical Industries, Inc.; CARBOPOLE 943, manufactured by Goodrich Co.), chitosan, sodium alginate and pectin. These polymers may be used alone, or powders of at least two of these polymers may be used as a mixture in an appropriate ratio. Among them, PEO, HPMC, HPC, CMC-Na and carboxyvinyl polymers may be preferably used as the gel-forming polymer.

A preferable example of the granule with controlled release of the biologically active substance includes a granule prepared by coating a core granule containing at least one biologically active substance with a controlled release film. For preparing such a dry-coated granule, a granule obtained by coating an inert carrier such as NONPAREIL [NONPAREIL-101 (particle diameter; 850-710, 710-500, 500-355 μm), NONPAREIL-103 (particle diameter; 850-710, 710-500, 500-355 μm), NONPAREIL-105 (particle diameter; 710-500, 500-355, 300-180 μm), manufactured by Freund Co.] or CELPHERE [CP-507 (particle diameter; 500-71.0 µm) or CP-305 (particle diameter; 300-500 µm), manufactured by Asahi Kasei Co.) as a core with the biologically active substance, or a particle prepared by granulating the biologically active substance and carrier such as an excipient conventionally used for producing pharmaceutical preparations can be used as a core granule. Such core granules can be produced, for example, by the method described in JP-A 63-301816. For example, when a core granule is obtained by coating a core of a inert carrier with the biologically active substance, core granules containing the biologically active substance can be prepared by wet granulation using a centrifugal fluidized bed granulation machine (CF-mini, CF-360, manufactured by Freund Co.) or a tumbling fluidized bed granulation machine (POWREX MP-10), but not limited to them. Alternatively, a core of an inert carrier may be coated by spraying the biologically active substance while adding a solution containing a binder and the like onto the core by spraying or the like. The granulation machine is not limited, and for example, it is preferable to use a centrifugal tumbling granulation machine in the latter coating method. A core may be coated with the biologically active substance in two steps by combining coating using the above-mentioned two granulation machines.

When a core granule containing the biologically active substance is produced using a centrifugal tumbling granulation machine, the feeding weight and/or the spraying or dusting speed of the spraying or dusting material as described above is preferably controlled.

When a core of an inert carrier is not used, a core granule is obtained by granulating an excipient such as lactose, white sugar, mannitol, corn starch or crystalline cellulose and the biologically active substance together with a binder such as hydroxypropylmethyl cellulose, hydroxypropyl cellulose, methyl cellulose, polyvinyl alcohol, MACROGOL, PLURONIC F68, gum Arabic, gelatin or starch, and optionally a disintegrant such as carboxymethyl cellulose sodium, carboxymethyl cellulose calcium, cross-carboxymethyl cellulose sodium (Ac-Di-Sol, manufactured by FMC International Co.), polyvinyl pyrrolidone or low substituted hydroxypropyl cellulose, using a stirring granulator, wet extrusion granulator or fluidized bed granulator.

The core granules thus obtained can be sieved to obtain particles having a desired size. The core granules may be prepared by dry granulation using a roller compactor. The core granules to be used have a size of 5 mm or less, preferably from 50 µm to 5 mm, more preferably from 100 µm to 3 mm, and further preferably from 200 µm to 2 mm.

The core granules containing the biologically active substance thus obtained may be further coated to provide an intermediate coating layer, and then the resulting particle may be used as a core granule. When the active pharmaceutical ingredient is a drug sensitive to acids such as PPI, it is preferable for improving the stability of a drug to block direct contact between the core granule containing the biologically active substance and a controlled release film by providing the intermediate coating layer. The intermediate coating layer may consist of plural layers.

An example of a coating material for the intermediate coating layer includes a blend of a polymer base such as low substituted hydroxypropyl cellulose, hydroxypropyl cellulose, hydroxypropylmethyl cellulose (such as TC-5), polyvinyl pyrrolidone, polyvinyl alcohol, methyl cellulose or hydroxyethylmethyl cellulose and sugar such as sucrose [refined white sugar such as pulverized sugar (powdered sugar) or non-pulverized sugar], starch sugar such as corn starch, lactose, honey or sugar alcohol (such as D-mannitol or erythritol) at an appropriate ratio. In addition, the intermediate coating layer may optionally contain an excipient (for example a masking agent (such as titanium oxide or the like) or an antistatic agent (such as titanium oxide, talc or the like) for formulation as described below.

The coating amount of the intermediate coating layer is usually from about 0.02 to about 1.5 parts by weight, preferably from about 0.05 to about 1 part by weight per 1 part by weight of the granule containing the active pharmaceutical ingredient. The coating may be performed by a conventional method. For example, it is preferable that ingredients for the intermediate coating layer are diluted with purified water or the like and then, the resulting liquid is sprayed to coat the core. A binder such as hydroxypropyl cellulose is preferably sprayed during the coating step.

The controlled release granule is preferably a granule having the controlled release coating film provided by coating the core granule with a coating material that pH-dependently dissolves/elutes to control release of a drug. The "pH-dependent" as used herein means that the biologically active substance is released by dissolution/elution at a predetermined pH or higher. While a conventional enteric coating film dissolves at about pH 5.5 and starts to release a drug, a coating material to be used in the present invention preferably dissolves at a higher pH (preferably from pH 6.0 to pH 7.5, more preferably from pH 6.5 to lower than pH 7.2) to suppress release of a drug in the stomach.

Examples of such a coating material for pH-dependently controlling release of the biologically active substance include polymers such as hydroxypropylmethyl cellulose phthalate (HP-55 and HP-50; manufactured by Shin-Etsu Chemical Co., Ltd.), cellulose acetate phthalate, carboxymethylethyl cellulose (CMEC, manufactured by Freund Co.), methyl methacrylate-methacrylic acid copolymers [EUDRAGIT L100 (methacrylic acid copolymer L) or EUDRAGIT S100 (methacrylic acid copolymer 3); manufactured by Rohm Co.], methacrylic acid-ethyl acrylate copolymers [EUDRAGIT L100-55 (dry methacrylic acid copolymer LD) or EUDRAGIT L30D-55 (methacrylic acid copolymer LD); manufactured by Rohm Co.], methacrylic acid-methyl acrylate-methyl methacrylate copolymers (EUDRAGIT FS30D; manufactured by Rohm Co.), hydroxypropyl cellulose acetate succinate (HPMCAS, manufactured by Shin-Etsu Chemical Co., Ltd.), polyvinyl acetate phthalate and shellac. The granule may have a plurality of controlled release coating films that release the biologically active substance under different conditions. The polymers as mentioned above as the coating material may be used alone or in a combination of two or more kinds, or two or more kinds of the polymers may be sequentially used for coating to form multiple layers. The coating materials are desirably used alone or in combination so that the resulting coating layer dissolves preferably at pH 6.0 or higher, more preferably at pH 6.5 or higher and further preferably at pH 6.75 or higher. It is also desirable to use a polymer soluble at pH 6.0 or higher in combination with a polymer soluble at pH 7.0 or higher. It is more desirable to use a polymer soluble at pH 6.0 or higher in combination with a polymer soluble at pH 7.0 or higher in a proportion from 1:0.5 to 1:5.

In coating, if necessary, a plasticizer, a stabilizer or the like, such as polyethyleneglycol, dibutyl sebacate, diethyl phthalate, triacetin or triethyl citrate may be used. The amount of the coating material is from 5% to 200%, preferably from 20% to 100%, and more preferably from 30% to 60% of the amount of the core granule. The dissolution rate of the biologically active substance from the biologically active substance-controlled release granule thus obtained is desirably 10% or less for 5 hours in a solution at pH 6.0, and 5% or less for 1 hour and 60% or more for 8 hours in a solution at pH 6.8.

The biologically active substance-controlled release granule thus obtained may be coated with a substance that becomes viscous on contact with water, such as polyethylene oxide (PEO, for example POLYOX WSR303 (molecular weight 7,000,000), POLYOX WSR Coagulant (molecular weight 5,000,000), POLYOX WSR 301 (molecular weight 4,000,000), Polyox WSR N-60K (molecular weight 2,000,000), POLYOX WSR 205 (molecular weight 600,000); manufactured by Dow Chemical Co.), hydroxypropylmethyl cellulose (HPMC; METLOSE 90SH10000, METLOSE 90SH50000, METLOSE 90SH30000, manufactured by Shin-Etsu Chemical Co., Ltd.), carboxymethyl cellulose (CMC-Na; SANLOSE F-1000MC), hydroxypropyl cellulose (HPC; for example HPC—H, manufactured by Nippon Soda Co.), hydroxyethyl cellulose (HEC), carboxyvinyl polymer (HIGHBIS WAKO (R) 103, 104, 105, manufactured by Wako Pure Chemical Industries, Inc.; CARBOPOLE 943, manufactured by Goodrich Co.), chitosan, sodium alginate or pectin, and the resulting coated granule may be used as a controlled release granule (hereinafter, simply referred to as the controlled release granule).

The controlled release granule may be formed by coating the core granule containing the biologically active substance with a diffusion-controlled film having an effect of controlling release of the biologically active substance by diffusion. Examples of the diffusion-controlled film include ethyl acrylate-methyl methacrylate-ethyl trimethylammonium chloride methacrylate copolymers [EUDRAGIT RS (aminoalkyl methacrylate copolymer RS) or EUDRAGIT RL (aminoalkyl methacrylate RL), manufactured by Rohm Co.], methyl methacrylate-ethyl acrylate copolymers (EUDRAGIT NE30D, manufactured by Rohm Co.) and ethyl cellulose. These films may be mixed in an appropriate proportion, or may be used as a mixture with a hydrophilic pore-forming material such as HPMC, HPC, a carboxyvinyl polymer, polyethyleneglycol 6000, lactose, mannitol or an organic acid in a given proportion.

For obtaining a controlled release granule that releases the biologically active substance after a given lag time, a layer of a disintegrant is provided between the core granule containing the biologically active substance and the controlled release coating film by coating the core granule with a swellable substance such as a disintegrant before coating the core granule with the diffusion-controlled film. For example, preferably, the core granule containing the biologically active substance is coated with a swellable substance such as cross-carmellose sodium (Ac-Di-Sol, manufactured by FMC International Co.), carmellose calcium (ECG505, manufactured by Gotoku Chemical Co.), cross-povidone (manufactured by ISP Inc.) or low substituted hydroxypropyl cellulose (L-HPC, manufactured by Shin-Etsu Chemical Co., Ltd.) as a first coating, and then coated with the diffusion-controlled film as a second coating, wherein the diffusion-controlled film is any one selected from an ethyl acrylate-methyl methacrylate-ethyl trimethylammonium chloride methacrylate copolymer (EUDRAGIT RS or EUDRAGIT RL, manufactured by Rohm Co.), a methyl methacrylate-ethyl acrylate copolymer (EUDRAGIT NE30D, manufactured by Rohm Co.) and ethyl cellulose, or a mixture of them, and mixed with a hydrophilic pore-forming substance such as HPMC, HPC, a carboxyvinyl polymer, polyethyleneglycol 6000, lactose, mannitol or an organic acid in a given proportion. Such second coating material may be an enteric polymer that pH-dependently releases the biologically active substance, such as hydroxypropylmethyl cellulose phthalate (HP-55, HP-50; manufactured by Shin-Etsu Chemical Co., Ltd.), cellulose acetate phthalate, carboxymethylethyl cellulose (CMEC, manufactured by Freund Co.), a methyl methacrylate-methacrylic acid copolymer [EUDRAGIT L100 (methacrylic acid copolymer L) or EUDRAGIT S100 (methacrylic acid copolymer S), manufactured by Rohm Co.], a methacrylic acid-ethyl acrylate copolymer [EUDRAGIT L100-55 (dry methacrylic acid copolymer LD) or EUDRAGIT L30D-55 (methacrylic acid copolymer LD), manufactured by Rohm Co.], a methacrylic acid-methyl acrylate-methyl methacrylate copolymer (EUDRAGIT FS30D, manufactured by Rohm Co.), hydroxypropyl cellulose acetate succinate (HPMCAS, manufactured by Shin-Etsu Chemical Co., Ltd.), polyvinyl acetate phthalate or shellac. The amount of the coating material is desirably from 1 to 200%, preferably from 20 to 100% and more preferably from 30 to 60% of the amount of the core granule.

In coating, if necessary, a plasticizer, a stabilizer or the like, such as polyethyleneglycol, dibutyl sebacate, diethyl phthalate, triacetin or triethyl citrate may be used. The biologically active substance-controlled release tablet, granule or fine granule thus obtained may be coated with a substance that becomes viscous on contact with water, such as polyethylene oxide [PEO, for example POLYOX WSR303 (molecular weight 7,000,000), POLYOX WSR Coagulant (molecular weight 5,000,000), POLYOX WSR 301 (molecular weight 4,000,000), Polyox WSR N-60K (molecular weight 2,000,000), POLYOX WSR 205 (molecular weight 600,000); manufactured by Dow Chemical Co.], hydroxypropylmethyl cellulose (HPMC; METLOSE 90SH10000, METLOSE 90SH50000, METLOSE 90SH30000, manufactured by Shin-Etsu Chemical Co., Ltd.), carboxymethyl cellulose (CMC-Na; SANLOSE F-1000MC), hydroxypropyl cellulose (HPC; for example HPC—H, manufactured by Nippon Soda Co.), hydroxyethyl cellulose (HEC), carboxyvinyl polymer (HIGHBIS WAKO (R) 103, 104, 105, manufactured by Wako Pure Chemical Industries, Inc.; CARBOPOLE 943, manufactured by Goodrich Co.), chitosan, sodium alginate or pectin, and the resulting coated granule may be used as a controlled release granule.

The granule having a plurality of the controlled release films that release the biologically active substance under different conditions may have a layer containing the biologically active substance between the controlled release coating films. An aspect of such multilayer structure containing the biologically active substance between the controlled release films includes a granule prepared by coating a granule in which release of the biologically active substance is controlled by means of the release control film with the biologically active substance, and then further coating the granule with the controlled release film.

Another aspect of the granule in which release of at least one biologically active substance is controlled may be a granule having the biologically active substance dispersed in a controlled release matrix. Such a controlled release granule can be produced by uniformly dispersing the biologically active substance in a hydrophobic carrier such as a wax including hardened caster oil, hardened rape oil, stearic acid and stearyl alcohol, or a polyglycerin fatty acid ester. The matrix refers to a composition containing the biologically active substance uniformly dispersed in a carrier, and an excipient usually used for producing pharmaceutical preparations such as lactose, mannitol, corn starch or crystalline cellulose may be optionally dispersed in the carrier together with the biologically active substance. Further, a powder of polyoxyethylene oxide, a cross-linked acrylic acid polymer (HIVISWAKO (R) 103, 104, 105, CARBOPOLE), HPMC, HPC, chitosan or the like that forms a viscous gel on contact with water may be dispersed in the matrix together with the biologically active substance and the excipient.

The granule can be prepared by spray drying, spray chilling or melt granulation.

The biologically active substance-controlled release granule thus obtained may be coated with a substance that becomes viscous on contact with water, such as polyethylene oxide [PEO, for example POLYOX WSR303 (molecular weight 7,000,000), POLYOX WSR Coagulant (molecular weight 5,000,000), POLYOX WSR 301 (molecular weight 4,000,000), Polyox WSR N-60K (molecular weight 2,000,000), POLYOX WSR 205 (molecular weight 600,000); manufactured by Dow Chemical Co.], hydroxypropylmethyl cellulose (HPMC; METLOSE 90SH10000, METLOSE 90SH50000, METLOSE 90SH30000, manufactured by Shin-Etsu Chemical Co., Ltd.), carboxymethyl cellulose (CMC-Na; SANLOSE F-1000MC), hydroxypropyl cellulose (HPC; for example HPC—H, manufactured by Nippon Soda Co.), hydroxyethyl cellulose (HEC), carboxyvinyl polymer (HIGHBIS WAKO (R) 103, 104, 105, manufactured by Wako Pure Chemical Industries, Inc.; CARBOPOLE 943, manufactured by Goodrich Co.), chitosan, sodium alginate or pectin, and the resulting coated granule may be used as a controlled release granule. The substance that becomes viscous on contact with water may be not only used for coating but also may be presented together with the granule in the same pharmaceutical preparation such as a capsule.

The controlled release granule may have various controlled release films and controlled release matrices as described above in combination.

The granule in which release of the biologically active substance is controlled has a size from 50 μm to 5 mm, preferably from 100 μm to 3 mm, and more preferably from 100 μm to 2 mm. The most preferable size of the granule is in the range form about 100 to about 1500 μm.

Further, additives including excipients (for example, glucose, fructose, lactose, sucrose, D-mannitol, erythritol, maltitol, trehalose, sorbitol, corn starch, potato starch, wheat starch, rice starch, crystalline cellulose, silicic anhydride, anhydrous calcium phosphate, precipitated calcium carbonate, calcium silicate and the like), binders (for example, hydroxypropyl cellulose, hydroxypropylmethyl cellulose, polyvinyl pyrrolidone, methyl cellulose, polyvinyl alcohol, carboxymethyl cellulose sodium, partial pregelatinized starch, pregelatinized starch, sodium alginate, pullulan, gum Arabic powder, gelatin and the like), disintegrants (for example, low substituted hydroxypropyl cellulose, carmellose, carmellose calcium, carboxymethyl starch sodium, cross-carmellose sodium, crospovidone, hydroxypropyl starch and the like), corrigents (for example, citric acid, ascorbic acid, tartaric acid, malic acid, aspartame, acesulfame potassium, thaumatin, saccharin sodium, glycyrrhizin dipotassium, sodium glutamate, sodium 5'-inosinate, sodium 5'-guanilate and the like), surfactants [for example, polysolbate (such as polysolbate 80), polyoxyethylene-polyoxypropylene copolymers, sodium laurylsulfate and the like], flavors (for example, lemon oil, orange oil, menthol, peppermint oil and the like), lubricants (for example, magnesium stearate, sucrose fatty acid esters, sodium fumarate stearate, stearic acid, talc, polyethyleneglycol and the like), colorants (for example, titanium oxide, edible yellow No. 5, edible blue No. 2, iron sesquioxide, yellow iron sesquioxide and the like), antioxidants (for example, sodium ascorbate, L-cysteine, sodium sulfite and the like), masking agents (for example, titanium oxide and the like) and antistatic agents (for example, talc, titanium oxide and the like) may be used for formulation.

The particle diameter of these materials used as these additives is not particularly limited, and it is preferably 500 μm or less from the viewpoint productivity and ease of administration.

The granule thus obtained may be directly administered as a mixture with a digestive tract-retentive gel-forming polymer, or may be formulated into a capsule by putting the granule in the capsule. The proportion of the digestive tract-retentive gel-forming polymer to the controlled release granule is desirably from 0.1% to 100%, preferably from 2% to 50%, more preferably from 10% to 40%, and further preferably from 10% to 35%.

The pharmaceutical composition thus obtained is a composition capable of sustaining the beneficial effect by means of such a controlled release system as exerts the therapeutic effect for at least 6 hours, preferably for 8 hours, more preferably for 12 hours and further preferably for 16 hours.

In producing the above-mentioned controlled release granule, the timing for heating the granule is not particularly limited, and the heating may be performed at any time of:
(1) during the granulation step for the core granules containing the biologically active substance;
(2) after the granulation step for the core granules containing the biologically active substance and before the step of coating with an optionally formed intermediate layer;
(3) during or after the step for coating with an optionally formed intermediate layer;
(4) before, during or after the step for coating the core granules with a controlled release coating film.

The timing for heating is preferably (2) after the granulation step for the core granules containing the biologically active substance and before the step of coating with an optionally formed intermediate layer; (3) during or after the step for coating with an optionally formed intermediate layer; or (4) before, during or after the step for coating the core granules with a controlled release coating film.

The controlled release coating film may be either a pH-dependent soluble controlled release coating film or a diffusion-controlled film, as described above. In the case of coating with a plurality of layers, the timing for heating may be before, during or after the coating step of each layer.

In the case of drying the granules after the coating step, the timing for heating may be before, during or after drying.

In the case of producing granules containing the biologically active substance dispersed in a controlled release matrix, the granules may be heated during or before dispersing the biologically active substance in the controlled release matrix, or may be heated before, during or after the subsequent coating step that is optionally performed.

In the case of applying the production method of the present invention to production of coated granules, the desirable temperature for heating and the desirable time for maintaining the granules at the said temperature after heating are the same as described above.

That is, the present invention encompasses:
(1) a method for producing coated granules containing a biologically active substance, which comprises, in a process for producing the granules, heating the temperature of the granules to about 50° C. or higher and then maintaining the granules at the said temperature for about 1 minute or longer;
(2) the method according to the above (1), wherein the coated granules containing a biologically active substance are dry coated granules;

(3) the method according to the above (1), wherein the coating of the coated granules comprises an intermediate coating layer formed on the core granules containing the biologically active substance;
(4) the method according to the above (1), wherein the coating of the coated granules comprises an enteric coating film formed on granules containing the biologically active substance;
(5) the method according to the above (1), wherein the coating of the coated granules comprises a controlled release coating film formed on granules containing the biologically active substance;
(6) the method according to the above (5), wherein the controlled release coating film is a pH-dependent soluble controlled release film;
(7) the method according to the above (6), wherein the pH-dependent soluble controlled release film is a controlled release film containing a polymer that dissolves at a pH range from 5.0 to 7.5;
(8) the method according to the above (7), wherein the polymer is a methacrylic acid copolymer;
(9) the method according to the above (5), wherein the controlled release coating film is a diffusion-controlled release coating film;
(10) the method according to the above (4), wherein the enteric coating film is formed with interposition of an intermediate coating layer formed on granules of an active pharmaceutical ingredient (granules containing the biologically active substance); and
(11) the method according to the above (5), wherein the controlled release coating film is formed with interposition of an intermediate coating layer formed on granules of an active pharmaceutical ingredient.

Examples of the biologically active substance that is preferably used in the production method of the present invention include, without depending on its drug efficacy range, benzimidazole proton pump inhibitors (PPI) represented by lansoprazole and optical isomers thereof (R-isomer and S-isomer, preferably R-isomer), omeprazole and optical isomers thereof (S-isomer: S-omeprazole), laveprazole and optical isomers thereof, pantoprazole and optical isomers thereof, and the like; and imidazopyridine PPI represented by tenatoprazole; which are therapeutic agents for gastritis, gastroesophageal reflux, gastric ulcer, duodenal ulcer and the like.

Specific examples of PPI include imidazole compounds such as ransoprazole and optical isomers thereof represented by the following formula (I'), benzoimidazole compounds represented by the formula (I), and imidazole compound derivatives (prodrug type PPI) represented by the formulae (II) and (III) or salts or optical isomers thereof.

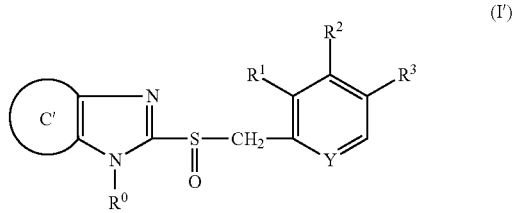

(I')

wherein, the ring C' represents an optionally substituted benzene ring or an optionally substituted aromatic monocyclic heterocyclic group; $R^0$ represents a hydrogen atom, an optionally substituted aralkyl group, an acyl group or an acyloxy group; $R^1$, $R^2$ and $R^3$ may be the same as or different from each other, and represent a hydrogen atom, an optionally substituted alkyl group, an optionally substituted alkoxy group or an optionally substituted amino group; and Y represents a nitrogen atom or CH.

Among compounds represented by the formula (I'), a compound in which the ring C' is an optionally substituted benzene ring is represented by the following formula (I):

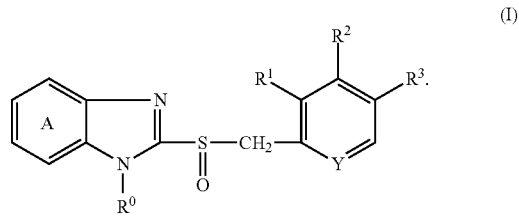

(I)

In the formula (I), the zing A represents an optionally substituted benzene ring, and $R^0$, $R^1$, $R^2$, $R^3$ and Y are as defined in the formula (I').

In a preferable compound of the formula (I), the ring A represents a benzene ring optionally substituted with substituent(s) selected from a halogen atom, an optionally halogenated $C_{1-4}$ alkyl group, an optionally halogenated $C_{1-4}$ alkoxy group and 5- to 6-membered heterocyclic groups; $R^0$ represents a hydrogen atom, an optionally substituted aralkyl group, an acyl group or an acyloxy group; $R^1$ represents a $C_{1-6}$ alkyl group, a $C_{1-6}$ alkoxy group, a $C_{1-6}$ alkoxy-$C_{1-6}$ alkoxy group, or a di-$C_{1-6}$ alkylamino group; $R^2$ represents a hydrogen atom, a $C_{1-6}$ alkoxy-$C_{1-6}$ alkoxy group or an optionally halogenated $C_{1-6}$ alkoxy group; $R^3$ represents a hydrogen atom or $C_{1-6}$ alkyl group; and Y represents a nitrogen atom.

A particularly preferable compound is a compound represented by the formula (Ia):

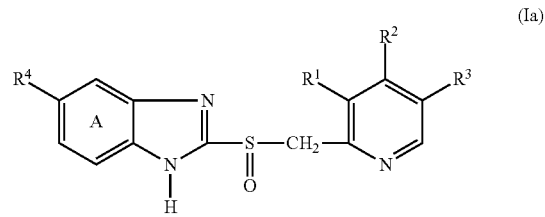

(Ia)

wherein, $R^1$ represents a $C_{1-3}$ alkyl group or a $C_{1-3}$ alkoxy group; $R^2$ represents a $C_{1-3}$ alkoxy group which is optionally halogenated or substituted with a $C_{1-3}$ alkoxy group; $R^3$ represents a hydrogen atom or a $C_{1-3}$ alkyl group; and $R^4$ represents a hydrogen atom, an optionally halogenated $C_{1-3}$ alkoxy group or a pyrrolyl group (for example a 1-, 2- or 3-pyrrolyl group).

A particularly preferable compound of the formula (Ia) is a compound in which $R^1$ is a $C_{1-3}$ alkyl group, $R^2$ is an optionally halogenated $C_{1-3}$ alkoxy group, $R^3$ is a hydrogen atom and $R^4$ is an optionally halogenated $C_{1-3}$ alkoxy group.

In the compound represented by the formula (I) (hereinafter, referred to as the compound (I)), examples of the "substituent" of the "optionally substituted benzene ring" represented by the ring A include halogen atoms, cyano groups, nitro groups, optionally substituted alkyl groups, hydroxyl groups, optionally substituted alkoxy groups, axyl groups, aryloxy groups, carboxyl groups, acyl groups, acyloxy groups, and 5- to 10-membered heterocyclic groups. The benzene ring may be substituted with 1 to 3 of these substituents. When the number of the substituents is 2 or more, they may be the same as or different from each other. Among them, preferable substituents are a halogen atom, an optionally substituted alkyl group and an optionally substituted alkoxy group.

Examples of the halogen atom include fluorine, chlorine and bromine, and fluorine is preferable among them.

Examples of the "alkyl group" of the "optionally substituted alkyl group" include $C_{1-7}$ alkyl groups (for example, methyl, ethyl, propyl, isopropyl, butyl, isobutyl, sec-butyl, tert-butyl, pentyl, hexyl, heptyl and the like). Examples of the "substituent" of the "optionally substituted alkyl group" include halogen atoms, a hydroxyl group, $C_{1-6}$ alkoxy groups (for example, methoxy, ethoxy, propoxy, butoxy and the like), $C_{1-6}$ alkoxy-carbonyl groups (for example, methoxycarbonyl, ethoxycarbonyl, propoxycarbonyl and the like) and a carbamoyl group. The alkyl group may be substituted with 1 to 3 of these substituents. When the number of the substituents is 2 or more, they may be the same as or different from each other.

Examples of the "alkoxy group" of the "optionally substituted alkoxy group" include $C_{1-6}$ alkoxy groups (for example, methoxy, ethoxy, propoxy, isopropoxy, butoxy, isobutoxy, pentoxy and the like). Examples of the "substituent" of the "optionally substituted alkoxy group)" are the same as those of the "substituent" of the "optionally substituted alkyl group", and the number of the substituent is also the same.

Examples of the "aryl group" include $C_{6-14}$ aryl groups (for example, phenyl, 1-naphthyl, 2-naphthyl, biphenyl, 2-anthryl and the like).

Examples of the "aryloxy group" include $C_{6-14}$ aryloxy groups (for example, phenyloxy, 1-naphthyloxy, 2-naphthyloxy and the like).

Examples of the "acyl group" include formyl, alkylcarbonyl, alkoxycarbonyl, carbamoyl, alkylcarbamoyl, alkylsulfinyl and alkylsulfonyl groups.

Examples of the "alkylcarbonyl group" include $C_{1-6}$ alkyl-carbonyl groups (for example, acetyl, propionyl and the like).

Examples of the "alkoxycarbonyl group" include $C_{1-6}$ alkoxy-carbonyl groups (for example, methoxycarbonyl, ethoxycarbonyl, propoxycarbonyl, butoxycarbonyl and the like).

Examples of the "alkylcarbamoyl group" include N—$C_{1-6}$ alkyl-carbamoyl groups (for example, methylcarbamoyl, ethylcarbamoyl and the like) and N,N-di-$C_{1-6}$ alkyl-carbamoyl groups (for example N,N-dimethylcarbamoyl, N,N-diethylcarbamoyl and the like).

Examples of the "alkylsulfinyl group" include $C_{1-7}$ alkylsulfinyl groups (for example methylsulfinyl, ethylsulfinyl, propylsulfinyl, isopropylsulfinyl and the like).

Examples of the "alkylsulfonyl group" include $C_{1-7}$ alkylsulfonyl groups (for example, methylsulfonyl, ethylsulfonyl, propylsulfonyl, isopropylsulfonyl and the like).

Examples of the "acyloxy group" include alkylcarbonyloxy groups, alkoxycarbonyloxy groups, carbamoyloxy groups, alkylcarbamoyloxy groups, alkylsulfonyloxy groups and alkylsulfonyloxy groups.

Examples of the "alkylcarbonyloxy group" include $C_{1-6}$ alkyl-carbonyloxy groups (for example, acetyloxy, propionyloxy and the like).

Examples of the "alkoxycarbonyloxy group" include $C_{1-6}$ alkoxy-carbonyloxy groups (for example, methoxycarbonyloxy, ethoxycarbonyloxy, propoxycarbonyloxy, butoxycarbonyloxy and the like).

Examples of the "alkylcarbamoyloxy group" include $C_{1-6}$ alkyl-carbamoyloxy groups (for example, methylcarbamoyloxy, ethylcarbamoyloxy and the like).

Examples of the "alkylsulfinyloxy group" include $C_{1-7}$ alkylsulfinyloxy groups (for example, methylsulfinyloxy, ethylsulfinuyloxy, propylsulfinyloxy, isopropylsulfinuyloxy and the like).

Examples of the "alkylsulfonyloxy group" include $C_{1-7}$ alkylsulfonyloxy groups (fox example, methylsulfonyloxy, ethylsulfonyloxy, propylsulfonyloxy, isopropylsulfonyloxy and the like).

Examples of the "5- to 10-membered heterocyclic group" include 5- to 10-membered (preferably 5- or 6-membered) heterocyclic groups containing at least one (for example 1 to 3) heteroatom selected from nitrogen, sulfur and oxygen atoms other than carbon atoms, and specific examples thereof include a 2- or 3-thienyl group, a 2-, 3- or 4-pyridyl group, a 2- or 3-furyl group, a 1-, 2- or 3-pyrrolyl group, a 2-, 3-, 4-, 5- or 8-quinolyl group, a 1-, 3-, 4- or 5-isoquinolyl group, and a 1-, 2- or 3-indolyl group. Among them, preferred is a 5- or 6-membered heterocyclic group such as a 1-, 2- or 3-pyrrolyl group.

The ring A is preferably a benzene ring that is optionally substituted with 1 or 2 substituents selected from halogen atoms, optionally halogenated $C_{1-4}$ alkyl groups, optionally halogenated $C_{1-4}$ alkoxy groups and 5- to 6-membered heterocyclic groups.

Examples of the "aromatic monocyclic heterocyclic ring" of the "optionally substituted aromatic monocyclic heterocyclic group" represented by the ring C' in the formula (I') include 5- to 6-membered aromatic monocyclic heterocyclic groups such as furan, thiophene, pyrrole, oxazole, isoxazole, thiazole, isothiazole, imidazole, pyrazole, 1,2,3-oxadiazole, 1,2,4-oxadiazole, 1,3,4-oxadiazole, furazan, 1,2,3-thiadiazole, 1,2,4-thiadiazole, 1,3,4-thiadiazole, 1,2,3-triazole, 1,2,4-triazole, Letrazole, pyridine, pyridazine, pyrimidine, pyrazine and triazine. Particularly preferable examples of the "aromatic monocyclic heterocyclic group" represented by the ring C' include the "optionally substituted benzene ring" represented by the ring A and "an optionally substituted pyridine ring". The "optionally substituted pyridine ring" represented by the ring C' may be substituted with 1 to 4 substituents that are the same as those of the "optionally substituted benzene ring" represented by the ring A, at substitutable positions.

The "aromatic monocyclic heterocyclic ring" of the "optionally substituted aromatic monocyclic heterocyclic group" is fused to the imidazole moiety at unlimited positions.

Examples of the "aralkyl group" of the "optionally substituted aralkyl group" represented by $R^0$ in the formula (I') or (I) include $C_{7-16}$ aralkyl groups (for example, $C_{6-10}$ aryl $C_{1-6}$ alkyl such as benzyl and phenethyl, and the like). Examples of the "substituent" of the "optionally substituted aralkyl group" are the same as those of the "substituent" of the "optionally substituted alkyl group", and the number of the substituents is 1 to 4. When the number of the substituents is 2 or more, they may be the same as or different from each other.

An example of the "acyl group" represented by $R^0$ is the "acyl group" described as a substituent for the ring A.

An example of the "acyloxy group" represented by $R^0$ is the "acyloxy group" described as a substituent for the ring A.

Preferably $R^0$ is a hydrogen atom.

An example of the "optionally substituted alkyl group" represented by $R^1$, $R^2$ or $R^3$ in the formula (I') or (I) is the "optionally substituted alkyl group" described as a substituent for the ring A.

An example of the "optionally substituted alkoxy group" represented by $R^1$, $R^2$ or $R^3$ is the "optionally substituted alkoxy group" described as a substituent for the ring A.

Examples of the "optionally substituted amino group" represented by $R^1$, $R^2$ or $R^3$ include an amino group, mono-$C_{1-6}$ alkylamino groups (for example, methylamino, ethylamino and the like), mono-$C_{6-14}$ arylamino groups (for example, phenylamino, 1-naphthylamino and 2-naphthylamino and the like), di-$C_{1-6}$ alkylamino groups (for example, dimethylamino, diethylamino and the like), and di-$C_{6-14}$ arylamino groups (for example, diphenylamino and the like).

Preferably $R^1$ is a $C_{1-6}$ alkyl group, a $C_{1-6}$ alkoxy group, a $C_{1-6}$ alkoxy-$C_{1-6}$ alkoxy group, or a di-$C_{1-6}$-alkylamino group. More preferably $R^2$ is a $C_{1-3}$ alkyl group or a $C_{1-3}$ alkoxy group.

Preferably $R^2$ is a hydrogen atom, a $C_{1-6}$ alkoxy-$C_{1-6}$ alkoxy group or an optionally halogenated $C_{1-6}$ alkoxy group. More preferably $R^3$ is a $C_{1-3}$ alkoxy group that is optionally halogenated or substituted with a $C_{1-3}$ alkoxy group.

Preferably $R^3$ is a hydrogen atom or a $C_{1-6}$ alkyl group. More preferably $R^3$ is a hydrogen atom or a $C_{1-3}$ alkyl group (particularly a hydrogen atom).

Preferably Y is a nitrogen atom.

Specific examples of the compound (I) include:
2-[[[3-methyl-4-(2,2,2-trifluoroethoxy)-2-pyridinyl]methyl] sulfinyl]-H-imidazole (lansoprazole),
2-[[(3,5-dimethyl-4-methoxy-2-pyridinyl)methyl]sulfinyl]-5-methoxy-1H-benzimidazole,
2-[[[4-(3-methoxypropoxy)-3-methyl-2-pyridinyl]methyl] sulfinyl]-1H-benzimidzole sodium salt,
5-difluoromethoxy-2-[[(3,4-dimethoxy-2-pyridinyl)methyl] sulfinyl]-1H-benzimidazole and the like.

Among these compounds, lansoprazole, i.e. 2-[[[3-methyl-4-(2,2,2-trifluoroethoxy)-2-pyridinyl]methyl]sulfinyl]-1H-benzimidazole is particularly preferable.

Besides PPI of the above-mentioned benzimidazole compounds, PPI of imidazopyridine compounds may be suitably used. An example of such PPI of imidazopyridine compounds is tenatoprazole.

The compound (I) and the compound (I') including imidazopyridine compounds may be racemic, or may be optically active compounds such as R-isomer or S-isomer. An optically active compound such as an optically active compound of lansoprazole, i.e. (R)-2-[[[3-methyl-4-(2,2,2-trifluoroethoxy)-2-pyridinyl]methyl]sulfinyl]-1H-benzimidazole or (S)-2-[[[3-methyl-4-(2,2,2-trifluoroethoxy)-2-pyridinyl]methyl]sulfinyl]-1H-benzimidazole is suitably used in the present invention. Although it is usually preferable that lansoprazole, (R)-lansoprazole or (S)-lansoprazole is used in the crystalline form, lansoprazole, it can be also used in the amorphous form because it is stabilized by being formulated into a pharmaceutical preparation as described below, and further stabilized by blending with a basic inorganic salt and by further providing an intermediate coating layer.

Salts of the compound (I') and the compound (I) are preferably pharmaceutically acceptable salts, and examples thereof include salts with inorganic bases, salts with organic bases and salts with basic amino acids.

Preferable examples of the salts with the inorganic salts include alkali metal salts such as sodium salts and potassium salts; alkali earth metal salts such as calcium salts and magnesium salts; and ammonium salts.

Preferable examples of the salts with the organic bases include salts with alkylamines (such as trimethylamine, triethylamine and the like), heterocyclic amines (such as pyridine, picoline and the like), alkanolamines (such as ethanolamine, diethanolamine, triethanolamine and the like), dicyclohexylamines, N,N'-dibenzylethylenediamine and the like.

Preferable examples of the salts with the basic amino acids include salts with arginine, lysine, ornithine and the like.

Alkali metal salts and alkali earth metal salts are preferable among them, and sodium salts are particularly preferable.

The compound (I') and the compound (1) can be produced by a per se known method, for example by the method described in JP-A 61-50978, U.S. Pat. No. 4,628,098, JP-A 10-195068, WO 98/21.201, JP-A 52-62275 or JP-A 54-141783 or a method similar thereto. The optically active compound (i) can be obtained by an optical resolution method (such as a fractional recrystallization method, a chiral column method, a diastereomer method and a method using a microbe or an enzyme), asymmetric oxidation or the like. The R-form of lansoprazole can be also produced, for example, according to the method described in WO 00/78745 or WO 01/83473.

Preferable examples of the benzimidazole compound having anti-ulcer effect used in the present invention include lansoprazole, omeprazole, rabeprazole, pantoprazole, leminoprazole and tenatoprazole (TU-199), and optically active compounds and pharmaceutically acceptable salts thereof. More preferred are lansoprazole and an optically active compound thereof, particularly R-isomer. Although lansoprazole or an optically active compound thereof, particularly R-isomer, is preferably crystalline, it may be amorphous. A prodrug of the PPI may be suitably used.

Preferable examples of the prodrug include prodrugs included in the compounds (I) and (I') as well as compounds represented by the following formulae (II) and (III).

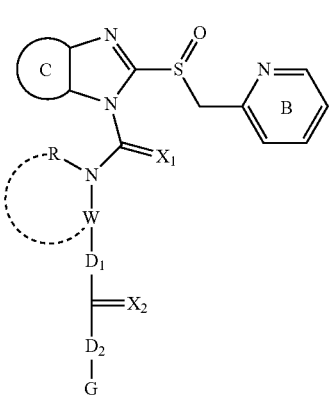

(II)

In the compound represented by the formula (II) (hereinafter, referred to as the compound (II)), the ring B represents "an optionally substituted pyridine ring".

The pyridine ring of the "optionally substituted pyridine ring" represented by the ring B may be substituted with 1 to 4 substituents at substitutable position(s). Examples of the substituent include halogen atoms (for example fluorine, chlorine, bromine, iodine and the like), optionally substituted hydrocarbon groups (for example, alkyl groups having 1 to 6 carbon atoms such as methyl, ethyl and n-propyl, and the like), optionally substituted amino groups (for example, amino groups that are mono- or di-substituted with alkyl group(s) having 1 to 6 carbon atoms, such as methylamino, dimethylamino, ethylamino and diethylamino, and the like), amide groups (for example, $C_{1-3}$ acylamino groups such as formamide and acetamide, and the like), optionally substituted lower alkoxy groups (for example, alkoxy groups having 1 to 6 carbon atoms such as methoxy, ethoxy, 2,2,2-trifluoroethoxy and 3-methoxypropoxy, and the like), and lower alkylenedioxy groups (for example, $C_{1-3}$ alkylenedioxy groups such as methylenedioxy and ethylenedioxy, and the like).

Examples of substituents which the substituent of the "optionally substituted pyridine ring" represented by the ring B may have include halogen atoms (for example fluorine, chlorine, bromine and iodine, and the like), lower alkyl groups (for example alkyl groups having 1 to 6 carbon atoms such as methyl, ethyl and propyl, and the like), lower alkenyl groups (for example alkenyl groups having 2 to 6 carbon atoms such as vinyl and allyl, and the like), lower alkynyl groups (for example alkynyl groups having 2 to 6 carbon atoms such as ethynyl and propargyl, and the like), cycloalkyl groups (for example cycloalkyl groups having 3 to 8 carbon atoms such as cyclopropyl, cyclobutyl, cyclopentyl and cyclohexyl, and the like), lower alkoxy groups (for example alkoxy groups having 1 to 6 carbon atoms such as methoxy and ethoxy, and the like), a nitro group, a cyano group, a hydroxyl group, a thiol group, a carboxyl group, lower alkanoyl groups (for example formyl; alkyl-carbonyl groups having 1 to 6 carbon atoms such as acetyl, propionyl and butyryl, and the like), lower alkanoyloxy groups (for example formyloxy; alkyl-carbonyloxy groups having 1 to 6 carbon atoms such as acetyloxy and propionyloxy, and the like), lower alkoxycarbonyl groups (for example alkoxy-carbonyl groups having 1 to 6 carbon atoms such as methoxycarbonyl, ethoxycarbonyl and propoxycarbonyl, and the like), aralkyloxy carbonyl groups (for example aralkyloxy-carbonyl groups having 7 to 11 carbon atoms such as benzyloxy carbonyl, and the like), aryl groups (for example aryl groups having 6 to 14 carbon atoms such as phenyl and naphthyl, and the like), aryloxy groups (for example aryloxy groups having 6 to 14 carbon atoms such as phenyloxy and naphthyloxy, and the like), arylcarbonyl groups (for example arylcarbonyl groups having 6 to 14 carbon atoms such as benzoyl and naphthoyl, and the like), arylcarbonyloxy groups (for example arylcarbonyloxy groups having 6 to 14 carbon atoms such as benzoyloxy and naphthoyloxy, and the like), optionally substituted carbamoyl groups (for example carbamoyl; carbamoyl groups which are mono- or di-substituted with alkyl having 1 to 6 carbon atoms such as methylcarbamoyl and dimethylcarbamoyl, and the like), and optionally substituted amino groups (for example amino; amino groups which are mono- or di-alkyl substituted with alkyl having 1 to 6 carbon atoms such as methylamino, dimethylamino, ethylamino and diethylamino, and the like). The number of the substituents and the substitution positions are not particularly limited.

The number of the substituents and the substitution positions of the "optionally substituted pyridine ring" represented by the ring B are not particularly limited, and the pyridine ring is preferably substituted with 1 to 3 of the above-mentioned substituents at any of the 3-, 4- and 5-positions.

The "optionally substituted pyridine ring" represented by the ring B is preferably 3-methyl-4-(2,2,2-trifluoroethoxy)-2-pyridyl.

In the present invention, the ring C denotes an "optionally substituted benzene ring" or an "optionally substituted aromatic monocyclic heterocyclic ring" which is fused to the imidazole moiety, and the former is preferable.

The benzene ring of the "optionally substituted benzene ring" represented by the ring C may be substituted with 1 to 4 substituents at substitutable positions, and examples of the substituents include halogen atoms (for example fluorine, chlorine, bromine and iodine, and the like), optionally substituted hydrocarbon groups (for example alkyl groups having 1 to 6 carbon atoms such as methyl, ethyl and n-propyl, and the like), optionally substituted amino groups (for example amino; amino groups which are mono- or di-substituted with alkyl having 1 to 6 carbon atoms such as methylamino, dimethylamino, ethylamino and diethylamino, and the like), amido groups (for example $C_{1-3}$ acylamino such as formamide and acetamide, and the like), optionally substituted lower alkoxy groups (for example alkoxy groups having 1 to 6 carbon atoms such as methoxy, ethoxy and difluoromethoxy, and the like), and lower alkylenedioxy groups (for example $C_{1-3}$ alkylenedioxy groups such as methylenedioxy and ethylenedioxy, and the like).

Examples of substituents which the substituent of the "optionally substituted benzene ring" represented by the ring C may have include halogen atoms (for example fluorine, chlorine, bromine and iodine, and the like), lower alkyl groups (for example alkyl groups having 1 to 6 carbon atoms such as methyl, ethyl and propyl, and the like), lower alkenyl groups (for example alkenyl groups having 2 to 6 carbon atoms such as vinyl and allyl, and the like), lower alkynyl groups (for example alkynyl groups having 2 to 6 carbon atoms such as ethynyl and propargyl, and the like), cycloalkyl groups (for example cycloalkyl groups having 3 to 8 carbon atoms such as cyclopropyl, cyclobutyl, cyclopentyl and cyclohexyl groups), lower alkoxy groups (for example alkoxy groups having 1 to 6 carbon atom(s) such as methoxy and ethoxy, and the like), a nitro group, a cyano group, a hydroxyl group, a thiol group, a carboxyl group, lower alkanoyl groups (for example formyl; alkyl-carbonyl groups having 1 to 6 carbon atoms such acetyl, propionyl and butyryl, and the like), lower alkanoyloxy groups (for example formyloxy; alkyl-carbonyloxy groups having 1 to 6 carbon atoms such as acetyloxy and propionyloxy, and the like), lower alkoxycarbonyl groups (for example alkoxy-carbonyl groups having 1 to 6 carbon atoms such as methoxycarbonyl, ethoxycarbonyl and propoxycarbonyl, and the like), aralkyloxycarbonyl groups (for example aralkyloxy-carbonyl groups having 7 to 17 carbon atoms such as benzyloxycarbonyl, and the like), aryl groups (for example aryl groups having 6 to 14 carbon atoms such as phenyl and naphthyl, and the like), aryloxy groups (for example aryloxy groups having 6 to 14 carbon atoms such as phenyloxy and naphthyloxy groups), arylcarbonyl groups (for example aryl-carbonyl groups having 6 to 14 carbon atoms such as benzoyl and naphthoyl groups), arylcarbonyloxy groups (for example aryl-carbonyloxy groups having 6 to 14 carbon atoms such as benzoyloxy and naphthoyloxy groups), optionally substituted carbamoyl groups (for example carbamoyl; carbamoyl groups which are mono- or di-substituted with alkyl having 1 to 6 carbon atoms such as methylcarbamoyl and dimethylcarbamoyl, and the like), and optionally substituted amino groups (for example amino; amino groups which are mono- or di-substituted with alkyl having 1 to 6 carbon atoms such as methylamino, dimethylamino, ethylamino and diethylamino groups). The number of the substituents and the substitution positions are not particularly limited.

The "optionally substituted benzene ring" represented by the ring C is preferably a benzene ring.

Examples of the "aromatic monocyclic heterocyclic ring" of the "optionally substituted aromatic monocyclic heterocyclic ring" represented by the ring C include 5- to 6-membered aromatic monocyclic heterocyclic groups such as furan, thiophene, pyrrole, oxazole, isoxazole, thiazole, isothiazole, imidazole, pyrazole, 1,2,3-oxadiazole, 1,2,4-oxadiazole, 1,3,4-oxuadiazole, furazan, 1,2,3-thiadiazole, 1,2,4-thiadiazole, 1,3,4-thiadiazole, 1,2,3-triazole, 1,2,4-triazole, tetrazole, pyridine, pyridazine, pyrimidine, pyrazine and triazine. The "aromatic monocyclic heterocyclic group" represented by the ring C is particularly preferably a pyridine ring. The "aromatic monocyclic heterocyclic group" represented by the ring C may be substituted with 1 to 4 substituents that are the same as those of "the optionally substituted benzene ring" represented by the ring C at substitutable positions.

The "aromatic monocyclic heterocyclic ring" of the "optionally substituted aromatic monocyclic heterocyclic group" is fused to the imidazole moiety at unlimited positions.

In the present invention, $X_1$ and $X_2$ each represent an oxygen atom or a sulfur atom. Preferably, both $X_1$ and $X_2$ represent an oxygen atom.

In the present invention, W represents an "optionally substituted divalent linear hydrocarbon group" or a divalent group represented by the formula:

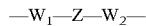

—$W_1$—Z—$W_2$—

[wherein, $W_1$ and $W_2$ each represent a "divalent linear hydrocarbon group" or a bond; and Z represents an "optionally substituted divalent hydrocarbon group", an "optionally substituted divalent heterocyclic group", an oxygen atom, $SO_n$ (wherein n represents 0, 1 or 2), or >N–E (wherein E represents a hydrogen atom, an optionally substituted hydrocarbon group, an optionally substituted heterocyclic group, a lower alkanoyl group, a lower alkoxycarbonyl group, an aralkyloxycarbonyl group, a thiocarbamoyl group, a lower alkylsulfinyl group, a lower alkylsulfonyl group, a sulfamoyl group, a mono-lower alkylsulfamoyl group, a di-lower alkylsulfamoyl group, an arylsulfamoyl group, an arylsulfinyl group, an arylsulfonyl group, an arylcarbonyl group or an optionally substituted carbamoyl group); and $W_1$ and $W_2$ each represent a "divalent linear hydrocarbon group" when Z represents an oxygen atom, $SO_n$ or >N–E). Preferably W is an "optionally substituted divalent linear hydrocarbon group".

Examples of the "divalent linear hydrocarbon group" of the "optionally substituted divalent linear hydrocarbon group" represented by W, and examples of the "divalent linear hydrocarbon group" represented by $W_1$ and $W_2$ include $C_{1-6}$ alkylene groups (for example methylene, ethylene and trimethylene, and the like), $C_{2-6}$ alkenylene groups (for example ethenylene and the like), and $C_{2-6}$ alkynylene groups (for example ethynylene and the like). The divalent linear hydrocarbon group of W may have 1 to 6 substituents that are the same as those of the "optionally substituted benzene ring" represented by the ring C at substitutable positions.

Preferable examples of the "divalent linear hydrocarbon group" of the "optionally substituted divalent linear hydrocarbon group" represented by W and the "divalent linear hydrocarbon group" represented by $W_1$ and $W_1$ include a methylene group and an ethylene group. Particularly W is preferably an ethylene group. When Z is an oxygen atom, $SO_n$, or >N–E (wherein n and E are as defined above), the "divalent linear hydrocarbon group" represented by $W_1$ is preferably a hydrocarbon group having two or more carbon atoms.

Examples of the "hydrocarbon ring" of the "optionally substituted divalent hydrocarbon ring group" represented by Z include aliphatic hydrocarbon rings and aromatic hydrocarbon rings, and among them, the rings having 3 to 16 carbon atoms are preferred. The hydrocarbon ring may be substituted with 1 to 4 substituents that are the same as those of the "optionally substituted benzene ring" represented by the ring C at substitutable positions. The hydrocarbon ring may be cycloalkane, cycloalkene, arene or the like.

Examples of the "cycloalkane" of the "optionally substituted divalent hydrocarbon ring group" represented by Z include preferably lower cycloalkane, and for example $C_{3-10}$ cycloalkane such as cyclopropane, cyclobutane, cyclopentane, cyclohexane, cycloheptane, cyclooctane, bicyclo[2.2.1]heptane or adamantine is usually used.

Examples of the "cycloalkene" of the "optionally substituted divalent hydrocarbon ring group" represented by Z include preferably lower cycloalkene, and for example $C_{4-9}$ cycloalkene such as cyclopropene, cyclobutene, cyclopentene, cyclohexene, cycloheptene or cyclooctene is usually used.

Examples of the "arene" of the "optionally substituted divalent hydrocarbon ring group" represented by Z include preferably $C_{6-14}$ arene such as benzene, naphthalene and phenanthrene, and for example phenylene is usually used.

Examples of the "heterocyclic group" of the "optionally substituted divalent heterocyclic group" represented by Z include 5- to 12-membered "aromatic heterocyclic groups" and "saturated or unsaturated non-aromatic heterocyclic groups" containing at least one (preferably 1 to 4, more preferably 1 or 2) of 1 to 3 kinds (preferably 1 or 2 kinds) of heteroatoms selected from oxygen, sulfur and nitrogen atoms as the atoms constituting the ring (ring atoms). The heterocyclic group may be substituted with 1 to 4 substituents that are the same as those of the "optionally substituted benzene ring" represented by the ring C.

Examples of the "aromatic heterocyclic group" of the "optionally substituted divalent heterocyclic group" represented by Z include aromatic monocyclic heterocyclic groups and aromatic fused heterocyclic groups.

Examples of the "aromatic monocyclic heterocyclic group" include 5- to 6-membered aromatic monocyclic heterocyclic groups such as furan, thiophene, pyrrole, oxazole, isoxazole, thiazole, isothiazole, imidazole, pyrazole, 1,2,3-oxadiazole, 1,2,4-oxadiazole, 1,3,4-oxadiazole, furazan, 1,2,3-thiadiazole, 1,2,4-thiadiazole, 1,3,4-thiadiazole, 1,2,3-triazole, 1,2,4-triazole, tetrazole, pyridine, pyridazine, pyrimidine, pyrazine and triazine.

Examples of the "aromatic fused heterocyclic group" include, 8- to 12-membered aromatic fused heterocyclic groups such as benzofuran, isobenzofuran, benzothiophene, isobenzothiophene, indole, isoindole, 1H-indazole, benzimidazole, benzoxazole, 1,2-benzoisoxazole, benzothiazole, 1,2-benzoisothiazole, 1H-benzotriazole, quinoline, isoquinoline, cinnoline, quinazoline, quinoxaline, phthalazine, naphthylidine, purine, pteridine, carbazole, calboline, acridine, phenoxazine, phenothiazine, phenazine, phenoxathiine, thianthrene, phenanthridine, phenanthroline, indolizine, pyrrolo[1,2-b]pyridazine, pyrazolo[1,5-a]pyridine, imidazo[1,2-a]pyridine, imidazo[1,5-a]pyridine, imidazo[1,2-b]pyridazine, imidazo[1,2-a]pyrimidine, 1,2,4-triazolo[4,3-a]pyridine and 1,2,4-triazolo[4,3-b]pyridazine.

Examples of the "saturated or unsaturated non-aromatic heterocyclic group" of the "optionally substituted divalent heterocyclic group" represented by Z include 3- to 6-membered (preferably 5- to 6-membered) saturated or unsaturated (preferably saturated) non-aromatic heterocyclic groups (aliphatic heterocyclic groups) such as oxirane, azetidine, oxetane, thietane, pyrrolidine, tetrahydrofuran, tetrahydrothiophene, piperidine, tetrahydropyrane, tetrahydrothiopyrane, morpholine, thiomorpholine, piperazine, azepane, oxepane, thiene, oxazepane, thiazepane, azocane, oxocane, thiocane, oxazocane and thiazocane. The saturated or unsaturated non-aromatic heterocyclic group may be oxo-substituted, and may be, for example, 2-oxoazetidine, 2-oxopyrrolidine, 2-oxopiperidine, 2-oxoazepane, 2-oxoazocane, 2-oxotetrahydrofuran, 2-oxotetrahydropyrane, 2-oxotetrahydrothiophene, 2-oxothiane, 2-oxopiperazine, 2-oxooxepane, 2-oxooxazepane, 2-oxothiepane, 2-oxothiazepane, 2-oxooxocane, 2-oxothiocane, 2-oxooxazocane, 2-oxothiazocane or the like.

The two bonds from the "hydrocarbon ring" of the "optionally substituted divalent hydrocarbon ring" or the "heterocyclic group" of the "optionally substituted divalent heterocyclic group" represented by Z may be present at any possible positions.

The "optionally substituted hydrocarbon group" and the "optionally substituted heterocyclic group" represented by E are as defined below.

Examples of the "lower alkanoyl group" represented by E include formyl and $C_{1-6}$ alkyl-carbonyl groups such as acetyl, propionyl, butyryl and isobutyryl.

Examples of the "lower alkoxycarbonyl group" represented by E include $C_{1-6}$ alkyloxy-carbonyl groups such as methoxycarbonyl, ethoxycarbonyl, propoxycarbonyl and butoxycarbonyl.

Examples of the "aralkyloxycarbonyl group" represented by E include $C_{7-11}$ aralkyloxy-carbonyl groups such as benzyloxycarbonyl.

Examples of the "lower alkylsulfinyl group" represented by E include $C_{1-6}$ alkylsulfinyl groups such as methylsulfinyl and ethylsulfinyl.

Examples of the "lower alkylsulfonyl group" represented by E include $C_{1-6}$ alkylsulfonyl groups such as methylsulfonyl and ethylsulfonyl.

Examples of the "mono-lower alkylsulfamoyl group" represented by E include mono-$C_{1-6}$ alkylsulfamoyl groups such as methylsulfamoyl and ethylsulfamoyl.

Examples of the "di-lower alkylsulfamoyl group" represented by E include di-$C_{1-6}$ alkylsulfamoyl groups such as dimethylsulfamoyl and diethylsulfamoyl.

Examples of the "arylsulfamoyl group" represented by E include $C_{6-10}$ arylsulfamoyl groups such as phenylsulfamoyl and naphthylsulfamoyl.

Examples of the "arylsulfinyl group" represented by E include $C_{6-10}$ arylsulfinyl groups such as phenylsulfinyl and naphthylsulfinyl.

Examples of the "arylsulfonyl group" represented by E include $C_{6-10}$ arylsulfonyl groups such as phenylsulfonyl and naphthylsulfonyl.

Examples of the "arylcarbonyl group" represented by E include $C_{6-10}$ arylcarbonyl groups such as benzoyl and naphthoyl.

Examples of the "optionally substituted carbamoyl group" represented by E include groups represented by the formula —CONR$_2$R$_3$ (wherein, R$_2$ and R$_3$ each represent a hydrogen atom, an optionally substituted hydrocarbon group or an optionally substituted heterocyclic group; or R$_2$ and R$_3$ may be taken together with the adjacent nitrogen atom to form a zing).

In the present invention, R represents an "optionally substituted hydrocarbon group" or an "optionally substituted heterocyclic group", or R may be linked to W. Preferably R is an optionally substituted $C_{1-6}$ hydrocarbon group, in particular, an optionally substituted lower ($C_{1-6}$) alkyl group. The "optionally substituted hydrocarbon group" and the "optionally substituted heterocyclic group" represented by R are as defined below. The case wherein R and W are linked to each other will be also described in detail hereinafter.

In the present invention, D$_1$ and D$_2$ each represent a bond, an oxygen atom, a sulfur atom or >NR$_1$, wherein R$_1$ represents a hydrogen atom or an optionally substituted hydrocarbon group, provided that a case where both D$_1$ and D$_2$ are bonds is excluded. Preferably D$_1$ and D$_2$ each are a bond or an oxygen atom, and it is particularly preferable that D$_1$ is an oxygen atom and D is an oxygen atom or a bond. The "optionally substituted hydrocarbon group" represented by R$_1$ is as defined below.

In the present invention, G represents an "optionally substituted hydrocarbon group" or an "optionally substituted heterocyclic group". Preferably G is an optionally substituted $C_{1-6}$ hydrocarbon group, or an optionally substituted saturated heterocyclic group containing 1 to 4 heteroatoms selected from oxygen, nitrogen and sulfur atoms as zing-constituting atoms. Particularly preferred is an optionally substituted $C_{1-6}$ hydrocarbon group, or an optionally substituted saturated oxygen-containing heterocyclic group optionally containing 1 to 3 heteroatoms selected from oxygen, nitrogen and sulfur atoms as ring-constituting atoms. The "optionally substituted hydrocarbon group" or the "optionally substituted heterocyclic group" represented by G is as defined below.

Examples of the "hydrocarbon group" of the "optionally substituted hydrocarbon group" represented by E, R, R$_1$ or G include saturated or unsaturated aliphatic hydrocarbon groups, saturated or unsaturated alicyclic hydrocarbon groups, saturated or unsaturated alicyclic-aliphatic hydrocarbon groups, aromatic hydrocarbon groups and aromatic-saturated or unsaturated alicyclic hydrocarbon groups, and these groups preferably has 1 to 16, more preferably 1 to 6 carbon atoms. Specific examples thereof include alkyl groups, alkenyl groups, alkynyl groups, cycloalkyl groups, cycloalkenyl groups, cycloalkylalkyl groups, cycloalkenylalkyl groups, aryl groups and arylalkyl groups.

Preferable examples of the "alkyl group" includes lower alkyl groups ($C_{1-6}$ alkyl groups), and for example, a $C_{1-6}$ alkyl group such as methyl, ethyl, propyl, isopropyl, butyl, isobutyl, sec-butyl, tert-butyl, pentyl, 1-ethylpropyl or hexyl is usually used. Preferably R is a lower alkyl group (a $C_{1-6}$ alkyl group), particularly preferably methyl.

Preferable examples of the "alkenyl group" include lower alkenyl groups, and for example, a $C_{2-7}$ alkenyl group such as vinyl, 1-propenyl, allyl, isopropenyl, butenyl, isobutenyl or 2,2-dimethyl-pent-4-enyl is usually used.

Preferable examples of the "alkynyl group" include lower alkynyl groups, and for example, a $C_{2-6}$ alkynyl group such as ethynyl, propargyl or 1-propinyl is usually used.

Preferable examples of the "cycloalkyl group" include lower cycloalkyl groups, and for example, a $C_{3-10}$ cycloalkyl group such as cyclopropyl, cyclobutyl, cyclopentyl, cyclohexyl, cycloheptyl, cyclooctyl, bicyclo[2.2.1]heptanyl or adamantyl is usually used.

Preferable examples of the "cycloalkenyl group" include lower cycloalkenyl groups, and for example, a $C_{3-10}$ cycloalkenyl group such as cyclopropenyl, cyclobutenyl, cyclopentenyl, cyclohexenyl, cycloheptenyl, cyclooctenyl or bicyclo[2.2.1]hept-5-ene-2-yl is usually used.

Preferable examples of the "cycloalkylalkyl group" include lower cycloalkylalkyl groups, and for example, a $C_{4-9}$ cycloalkylalkyl group such as cyclopropylmethyl, cyclopropylethyl, cyclobutylmethyl, cyclopentylmethyl, cyclohexylmethyl or cyclohexylethyl is usually used.

Preferable examples of the "cycloalkenylalkyl group" include lower cycloalkenylalkyl groups, and for example, a $C_{4-9}$ cycloalkenylalkyl such as cyclopentenylmethyl, cyclohexenylmethyl, cyclohexenylethyl, cyclohexenylpropyl, cycloheptenylmethyl, cycloheptenylethyl or bicyclo[2.2.1]hept-5-ene-2-ylmethyl is usually used.

Preferable examples of the "aryl group" include $C_{1-6}$ aryl groups such as phenyl, 1-naphthyl, 2-naphthyl, biphenyl and 2-anthryl, and for example, a phenyl group is usually used.

The "arylalkyl group" has the above-defined "aryl group" as the aryl moiety and the above-defined "alkyl group" as the alkyl moiety. For example, the "arylalkyl group" is preferably a $C_{6-14}$ aryl-$C_{1-6}$ alkyl group, and for example, benzyl, phenethyl or the like is usually used.

Examples of substituents which the "hydrocarbon group" of the "optionally substituted hydrocarbon group" represented by E, R, $R_1$ or G may have include halogen atoms (for example fluorine, chlorine, bromine, iodine atoms, and the like), a nitro group, a cyano group, a hydroxyl group, a thiol group, a sulfa group, a sulfino group, a phosphono group, optionally halogenated lower alkyl groups (for example $C_{1-6}$ alkyl such as methyl, ethyl, propyl, isopropyl, butyl, isobutyl, sec-butyl, tert-butyl, pentyl, 1-ethylpropyl and hexyl; and mono-, di- or tri-hanogeno-$C_{1-6}$ alkyl groups such as chloromethyl, dichloromethyl, trichloromethyl, fluoromethyl, difluoromethyl, trifluoromethyl, 2-bromoethyl, 2,2,2-trifluoroethyl, pentafluoroethyl, 3,3,3-trifluoropropyl, 4,4,4-trifluorobutyl, 5,5,5-trifluoropentyl and 6,6,6-trifluorohexyl, and the like), an oxo group, an amidino group, an imino group, alkylenedioxy groups (for example $C_{1-3}$ alkylenedioxy groups such as methylenedioxy and ethylenedioxy, and the like), lower alkoxy groups (for example $C_{1-6}$ alkoxy groups such as methoxy, ethoxy, propoxy, isopropoxy, butoxy, isobutoxy, pentyloxy and hexyloxy, and the like), optionally halogenated lower alkyl groups (for example mono-, di- or tri-halogeno-$C_{1-6}$ alkoxy groups such as chloromethyloxy, dichloromethyloxy, trichloromethyloxy, fluoromethyloxy, difluoromethyloxy, trifluoromethyloxy, 2-bromoethyloxy, 2,2,2-trifluoroethyloxy, pentafluoroethyloxy, 3,3,3-trifluoropropyloxy, 4,4,4-trifluorobutyloxy, 5,5,5-trifluoropentyloxy and 6,6,6-trifluorohexyloxy, and the like), lower alkylthio groups (for example $C_{3-6}$ alkylthio groups such as methylthio, ethylthio, propylthio isopropylthio, butylthio, isobutylthio, penthylthio and hexylthio), a carboxyl group, lower alkanoyl groups (for example formyl; $C_{1-6}$ alkyl-carbonyl groups such as acetyl, propionyl, butyryl and isobutyryl groups, and the like), lower alkanoyloxy groups (for example formyloxy; $C_{1-6}$ alkyl-carbonyloxy groups such as acetyloxy, propionyloxy, butyryloxy and isobutyryloxy, and the like), lower alkoxycarbonyl groups (for example $C_{1-6}$ alkoxycarbonyl groups such as methoxycarbonyl, ethoxycarbonyl, propoxycarbonyl and butoxycarbonyl, and the like), aralkyloxycarbonyl groups (for example $C_{7-11}$ aralkyloxy-carbonyl groups such as benzyloxycarbonyl, and the like), a thiocarbamoyl group, lower alkylsulfinyl groups (for example $C_{1-G}$ alkylsulfinyl groups such as methylsulfinyl and ethylsulfinyl, and the like), lower alkylsulfonyl groups (for example $C_{1-6}$ alkylsulfonyl groups such as methylsulfonyl and ethylsulfonyl, and the like), a sulfamoyl group, mono-lower alkylsulfamoyl groups (for example mono-$C_{1-6}$ alkylsulfamoyl groups such as methylsulfamoyl and ethylsulfamoyl, and the like), di-lower alkylsulfamoyl groups (for example di-$C_{1-6}$ alkylsulfamoyl groups such as dimethylsulfamoyl and diethylsulfamoyl, and the like), arylsulfamoyl groups (for example $C_{6-10}$ arylsulfamoyl groups such as phenylsulfamoyl and naphthylsulfamoyl, and the like), aryl groups (for example $C_{6-10}$ aryl groups such as phenyl and naphthyl, and the like), aryloxy groups (for example $C_{6-10}$ aryloxy groups such as phenyloxy and naphthyloxy, and the like), arylthio groups (for example $C_{6-10}$ arylthio groups such as phenylthio and naphthylthio, and the like), aryl sulfinyl groups (for example $C_{6-10}$ arylsulfinyl groups such as phenylsulfinyl and naphthylsulfinyl, and the like), arylsulfonyl groups (for example $C_{6-10}$ arylsulfonyl groups such as phenylsulfonyl and naphthylsulfonyl, and the like), arylcarbonyl groups (for example $C_{6-10}$ aryl-carbonyl groups such as benzoyl and naphthoyl, and the like), arylcarbonyloxy groups (for example $C_{6-10}$ aryl-carbonyloxy groups such as benzoyloxy and naphthoyloxy, and the like), optionally halogenated lower alkylcarbonylamino groups (for example optionally halogenated $C_{6-10}$ alkyl-carbonylamino groups such as acetylamino and trifluoroacetylamino, and the like), optionally substituted carbamoyl groups (for example groups represented by the formula —$CONR_2R^3$ (wherein, $R_2$ and $R_3$ each represent a hydrogen atom, an optionally substituted hydrocarbon group or an optionally substituted heterocyclic group, or $R_2$ and $R_3$ may be taken together with the adjacent nitrogen atom to form a ring)), an optionally substituted amino groups (for example groups represented by the formula —$NR^2R_3$ (wherein, $R_2$ and $R_3$ are as defined above, or $R_2$ and $R_3$ may be taken together with the adjacent nitrogen atom to form a ring)), optionally substituted ureido groups (for example, groups represented by the formula —$NHCONR_2R^3$ (wherein, $R_2$ and $R_3$ are as defined above, or $R_2$ and $R_3$ may be taken together with the adjacent nitrogen atom to form a ring)), optionally substituted carboxamide groups (for example, the groups represented by the formula. —$NR_2COR_3$ (wherein, $R_2$ and $R_3$ are as defined above)), optionally substituted sulfonamide groups (for example, groups represented by the formula —$NR_2SO_2R_3$ (wherein, $R_2$ and $R_3$ are as defined above)), and optionally substituted heterocyclic groups (which are as defined for above $R_2$ and $R_3$).

Examples of the "hydrocarbon group" of the "optionally substituted hydrocarbon group" in $R_2$ or $R_3$ include lower alkyl groups (for example alkyl groups having 1 to 6 carbon atoms such as methyl, ethyl and propyl, and the like), lower alkenyl groups (for example alkenyl groups having 2 to 6 carbon atoms such as vinyl and allyl, and the like), lower alkynyl groups (for example alkynyl groups having 2 to 6 carbon atoms such as ethynyl and propargyl, and the like), cycloalkyl groups (for example cycloalkyl groups having 3 to 8 carbon atoms such as cyclopropyl, cyclobutyl, cyclopentyl and cyclohexyl, and the like), cycloalkenyl groups (for example cycloalkeny groups having 3 to 8 carbon atoms such as cyclobutenyl, cyclopentenyl and cyclohexenyl, and the like), cycloalkylalkyl groups (for example $C_{3-6}$ cycloalkyl-$C_{1-6}$ alkyl groups such as cyclopropylmethyl, cyclobutylmethyl, cyclopentylmethyl and cyclohexylmethyl, and the like), cycloalkenylalkyl groups (for example $C_{3-6}$ cycloalkenyl-$C_{1-6}$ alkyl such as cyclobutenylmethyl, cyclopentenylmethyl and cyclohexenylmethyl, and the like), aryl groups (for example aryl groups having 6 to 14 carbon atoms such as phenyl and naphthyl, and the like), and arylalkyl groups (for example $C_{6-14}$ aryl-$C_{1-6}$ alkyl such as benzyl and naphthylmethyl, and the like).

Examples of the "heterocyclic group" of the "optionally substituted heterocyclic group" represented by $R_2$ or $R_3$ include 5- to 12-membered, monocyclic or fused heterocyclic groups having 1 to 4 heteroatoms of 1 or 2 kinds selected from nitrogen, sulfur and oxygen atoms, such as pyridyl, pyrrolidinyl, piperadinyl, piperizinyl, 2-oxoazepinyl, furyl, decahydroisoquinolinyl, quinolinyl, indolyl, isoquinolyl, thienyl, imidazolyl and morpholinyl. Examples of substituents for the "optionally substituted hydrocarbon group" and the "optionally substituted heterocyclic group" in $R_2$ or $R_3$ include halogen atoms (for example fluorine, chlorine, bromine, iodine, and the like), lower alkyl groups (for example alkyl groups having 1 to 6 carbon atoms such as methyl, ethyl and propyl, and the like), lower alkenyl groups (for example alkenyl groups having 2 to 6 carbon atoms such as vinyl and allyl, and the like), lower alkynyl groups (for example alkynyl groups having 2 to 6 carbon atoms such as ethynyl and propargyl, and the like), cycloalkyl groups (for example cycloalkyl groups having 3 to 8 carbon atoms such as cyclopropyl, cyclobutyl, cyclopentyl and cyclohexyl, and the like), lower alkoxy groups (for example alkoxy groups having 1 to 6 carbon atoms such as methoxy and ethoxy, and the like), a nitro group, a cyano group, a hydroxy group, a thiol group, a carboxyl group, lower alkanoyl groups (for example, formyl; alkyl-carbonyl groups having 1 to 6 carbon atoms such as acetyl, propionyl and butyryl, and the like), lower alkanoyloxy groups (for example formyloxy; alkyl-carbonyloxy groups having 1 to 6 carbon atoms such as acetyloxy and propionyloxy, and the like), lower alkoxycarbonyl groups (for example alkoxy-carbonyl groups having 1 to 6 carbon atoms such as methoxycarbonyl, ethoxycarbonyl and propoxycarbonyl, and the like), aralkyloxycarbonyl groups (for example aralkyloxy-carbonyl groups having 7 to 17 carbon atoms such as benzyloxycarbonyl, and the like), aryl groups (for example aryl groups having 6 to 14 carbon atoms such as phenyl and naphthyl, and the like), aryloxy groups (for example aryloxy groups having 6 to 14 carbon atoms such as phenyloxy and naphthyloxy, and the like), arylcarbonyl groups (for example aryl-carbonyl groups having 6 to 14 carbon atoms such as benzoyl and naphthoyl, and the like), arylcarbonyloxy groups (for example aryl-carbonyloxy groups having 6 to 14 carbon atoms such as benzoyloxy and naphthoyloxy, and the like), optionally substituted carbamoyl groups (for example carbamoyl; carbamoyl groups which are mono- or di-substituted with alkyl having 1 to 6 carbon atoms, such as methylcarbamoyl and dimethylcarbamoyl; and the like), and optionally substituted amino groups (for example amino; and amino groups which are mono- or di-substituted with alkyl having 1 to 6 carbon atoms, such as methylamino, dimethylamino, ethylamino and diethylamino; and the like). The number and substitution positions of substituents are not particularly limited.

Examples of the ring formed by $R_2$ and $R_3$ together with the adjacent nitrogen atom include pyrrolidine, piperidine, homopiperidine, morpholine, piperazine, tetrahydroquinoline and tetrahydroisoquinoline.

The "hydrocarbon group" of the "optionally substituted hydrocarbon group" represented by E, R, $R_1$ or G may have 1 to 5, preferably 1 to 3 of the above-mentioned substituents at substitutable positions. When the substituent number is 2 or more, the substituents may be the same or different.

Examples of the "heterocyclic group" of the "optionally substituted heterocyclic group" represented by E, R or G include 5 to 12-membered aromatic heterocyclic groups or saturated or unsaturated non-aromatic heterocyclic groups, which have at least one (preferably 1 to 4, more preferably 1 to 3) heteroatom of 1 to 3 kinds (preferably 1 or 2 kinds) selected from oxygen, sulfur, nitrogen and the like as ring-constituting atoms (ring atoms). The "heterocyclic group" of the "optionally substituted heterocyclic group" represented by G is, as described above, preferably a saturated oxygen-containing heterocyclic group, particularly a 5 to 12-membered saturated oxygen-containing heterocyclic group, which has 1 to 4 heteroatoms, more preferably 1 to 3 heteroatoms selected from oxygen, sulfur, nitrogen and the like as the ring atoms.

Examples of the "aromatic heterocyclic group" include aromatic monocyclic heterocyclic groups and aromatic fused heterocyclic groups.

Examples of the "aromatic monocyclic heterocyclic group" include 5- or 6-membered aromatic monocyclic heterocyclic groups such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl 1,2,3-triazolyl, 1,2,4-triazoyl, tetrazolyl, pyridyl, pyridazinyl, pyrimidinyl, pyrazinyl and triazinyl.

Examples of the "aromatic fused heterocyclic group" include 8- to 12-membered aromatic fused heterocyclic groups (preferably heterocyclic groups formed by fusing the above-mentioned 5- or 6-membered aromatic monocyclic heterocyclic group to a benzene ring, or heterocyclic groups formed by fusing identical or different two heterocyclic groups of the above-mentioned 5- or 6-membered aromatic monocyclic heterocyclic groups), such as benzofuranyl, isobenzofuranyl, benzothienyl, isobenzothienyl, indolyl, isoindoryl, 1H-indazolyl, benzimidazolyl, benzoxazolyl, 1,2,-benzoisoxazolyl, benzothiazolyl, 1,2-benzoisothiazolyl, 1H-benzotriazolyl, quinolyl, isoquinolyl, cinnolynyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl and 1,2,4-triazolo[4,3-b]pyridazinyl.

Examples of the "saturated or unsaturated non-aromatic heterocyclic group" include 3- to 8-membered (preferably 5- to 6-membered) saturated or unsaturated (preferably saturated) non-aromatic heterocyclic groups (aliphatic heterocyclic groups) such as oxiranyl, azetidinyl, oxetanyl, thietanyl, pyrrolidinyl, tetrahydrofuryl, thiolanyl, piperidinyl, tetrahydropyranyl, thianyl, morpholinyl, thiomorpholinyl, piperazinyl, azepanyl, oxepanyl, thiepanyl, oxazepanyl, thiazepanyl, azocanyl, oxocanyl, thiocanyl, oxazocanyl and thiazocanyl. These groups may be oxo-substituted, and examples thereof include 2-oxoazetidinyl, 2-oxopyrrolidinyl, 2-oxopiperidinyl, 2-oxoazepanyl, 2-oxoazocanyl, 2-oxotetrahydrofuryl, 2-oxotetrahydropyranyl, 2-oxothiolanyl, 2-oxothianyl, 2-oxopiperazinyl, 2-oxooxepanyl, 2-oxooxazepanyl, 2-oxothiepanyl, 2-oxothiazepanyl, 2-oxooxocanyl, 2-oxothiocanyl, 2-oxooxazocanyl and 2-oxothiazocanyl. Preferred is a 5-membered non-aromatic heterocyclic group such as 2-oxopyrrolidinyl.

Examples of substituents which the "heterocyclic group" of the "optionally substituted heterocyclic group" represented by E, R or G are the same as the "substituents" of the "optionally substituted hydrocarbon group" represented by E, R, $R_1$ or G.

The "heterocyclic group" of the "optionally substituted heterocyclic group" represented by E, R or G may have 1 to 5, preferably 1 to 3 of the above-mentioned substituents at substitutable positions of the heterocyclic group, and the substituents may be the same or different when the substituent number is 2 or more.

The case wherein R and W are linked to each other in the compound of the present invention is described below. When R and W are linked to each other, the position of linking between R and W is not particularly limited so long as the position is a linkable position in each of R and W.

The linkable position in R may be a linkable position in the "hydrocarbon group" or "substituent" of the "optionally substituted hydrocarbon group" represented by R, or a linkable position in the "heterocyclic group" or "substituent" of the "optionally substituted heterocyclic group" represented by R.

The linkable position in W may be a linkable position in the "divalent linear hydrocarbon group" of the "optionally substituted divalent linear hydrocarbon group" represented by W, a linkable position in the "divalent linear hydrocarbon group" represented by $W_1$ or $W_2$, a likable position in the "hydrocarbon ring" of the "optionally substituted hydrocarbon ring" represented by Z, or a linkable position in the "heterocyclic ring" of the "optionally substituted heterocyclic ring" represented by Z.

R and W may be linked to each other at respective linkable positions and taken together with the adjacent nitrogen atom to form a ring. Examples of the ring include saturated nitrogen-containing rings (for example, azetidine, pyrrolidine, piperidine, homopiperidine, and the like), unsaturated nitrogen-containing rings (for example, tetrahydropyridine, and the like), aromatic nitrogen-containing rings (for example, pyrrole, and the like), hetero-rings containing at least one hetero atom selected from the group consisting of nitrogen, oxygen and sulfur in addition to the nitrogen atom to which R and W are adjacent (for example, piperazine, morpholine, and the like), fused rings (for example, indole, indoline, isoindole, isoindoline, tetrahydroquinoline, tetrahydroisoquinoline, and the like). Among them, 4- to 7-membered rings are preferable.

The ring formed by linking F and W to each other at respective linkable positions together with the adjacent nitrogen atom may be substituted with 1 to 4 substituents at substitutable positions. When the number of the substituents is 2 or more, they may be the same as or different from each other. Examples of the substituent include substituents for the "optionally substituted hydrocarbon group" and "optionally substituted heterocyclic group" represented by R, and substituents for the "optionally substituted divalent linear hydrocarbon group" represented by W. Specific examples of the substituent include halogen atoms (for example fluorine, chlorine, bromine, iodine, and the like), and $C_{1-6}$ alkyl groups such as methyl, ethyl, propyl, isopropyl, butyl, isobutyl, sec-butyl, tert-butyl, pentyl, 1-ethylpropyl and hexyl.

The linking of R and W provides, for example, any one of the following moieties:

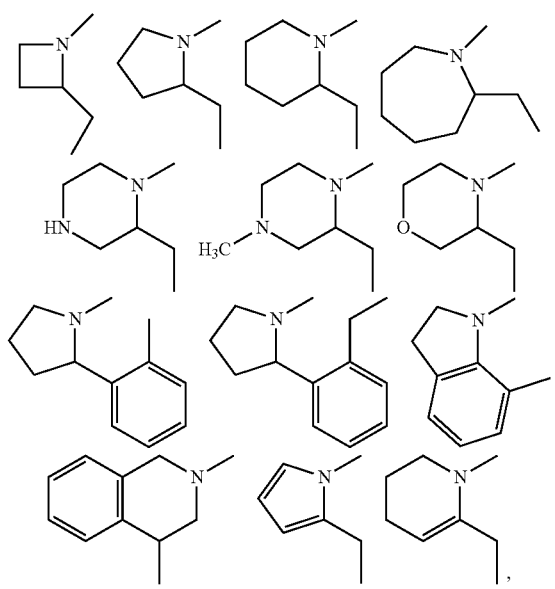

but not limited to them. It will be appreciated by those skilled in the art that these moieties may have substituent(s) as defined above, and may include isomers.

In the present invention, X represents a leaving group such as a halogen atom, a benzotriazolyl group or a (2,5-dioxypyrzolidin-1-yl) oxy group, preferably a halogen atom such as fluorine, chlorine, bromine or iodine, more preferably chlorine.

In the present invention, M represents a hydrogen atom, a metal cation or a quaternary ammonium ion.

Examples of the "metal cation" as used in the present invention include alkali metal ions (such as $Na^+, K^+, Li^+, Cs^+$, and the like), and $Na^+$ is preferable among them.

Examples of the "quaternary ammonium ion" as used in the present invention include a tetramethyl ammonium ion, a tetraethyl ammonium ion, a tetrapropyl ammonium ion and a tetrabutyl ammonium ion, and a tetrabutyl ammonium ion is preferable among them.

The compound (II) can a pharmacologically acceptable base salt via an acidic group in the molecule with an inorganic or organic base or the like, or a pharmacologically acceptable acid addition salt via a basic group in the molecule with an inorganic or organic acid or the like.

Examples of the inorganic base salt of the compound (II) include salts with alkali metals (such as sodium, potassium, and the like), alkali earth metals (such as calcium, and the like), ammonia, and the like. Examples of the organic base salt of the compound (II) include salts with dimethylamine, triethylamine, piperazine, pyrrolidine, piperidine, 2-phenyl-ethylamine, benzylamine, ethanolamine, diethanolamine, pyridine, collidine, and the like.

Examples of the acid addition salt of the compound (II) include inorganic acid salts (for example, hydrochloride, sulfate, hydrobromate, phosphate, and the like) and organic acid salts (for example, acetate, trifluoroacetate, succinate, maleate, fumarate, propionate, citrate, tartrate, lactate, oxalate, methanesulfonate, p-toluenesulfonate, and the like).

The compound (II) of the present invention may be a hydrate. The "hydrate" includes 0.5 to 5.0 hydrates, and preferred are a 0.5 hydrate, a 1.0 hydrate, a 1.5 hydrate and a 2.0 hydrate.

The compound (II) of the present invention includes racemates and optically active compounds. The optically active compound has an enantiomeric excess (e.e.) of preferably 90% or more, more preferably 99% or more based on one of the enantiomers. The optically active compound is preferably (R)-isomer represented by the following formula:

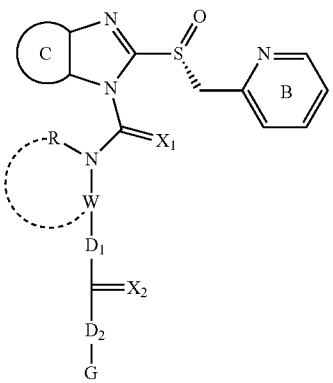

wherein symbols are as defined above.

Specific preferable examples of the compound (II) include:
2-[methyl[[((R)-2-[[[3-methyl-4-(2,2,2-trifluoroethoxy)-2-pyridyl]methyl]sulfinyl]-1H-benzimidazol-1-yl]carbonyl]amino]ethyl acetate;

2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl trimethylacetate;
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl cyclohexanecarboxylate;
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl benzoate;
2-[methyl[[2-[[[3-methyl-4-(2,2,2-trifluoroethoxy)-2-pyridyl]methyl]sulfinyl]-1H-benzimidazol-1-yl]carbonyl]amino]ethyl benzoate;
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl 4-methoxybenzoate;
2-[methyl[[(R)-2-[[[3-methyl-4-(2,2,2-trifluoroethoxy)-2-pyridyl]methyl]sulfinyl]-1H-benzimidazo-1-yl]carbonyl]amino]ethyl 3-chlorobenzoate;
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl 3,4-difluorobenzoate;
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl 4-trifluoromethoxybenzoate;
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl 4-fluorobenzoate;
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl 3,4,5-trimethoxybenzoate;
2-[methyl[[((R)-2-[[[3-methyl-4-(2,2,2-trifluoroethoxy)-2-pyridyl]methyl]sulfinyl]-1H-benzimidazol-1-yl]carbonyl]amino]ethyl 2-pyridinecarboxylate;
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl methoxyacetate;
ethyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate;
isopropyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate;
isopropyl 2-[methyl[[2-[[[3-methyl-4-(2,2,2-trifluoroethoxy)-2-pyridyl]methyl]sulfinyl]-1H-benzimidazol-1-yl]carbonyl]amino]ethyl carbonate;
benzyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate;
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl tetrahydropyran-4-yl carbonate;
2-methoxyethyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate;
2-[ethyl[[(R)-2-[[[3-methyl-4-(2,2,2-trifluoroethoxy)-2-pyridyl]methyl]sulfinyl]-1H-benzimidazol-1-yl]carbonyl]amino]ethyl acetate;
2-[isopropyl[[(R)-2-[[[3-methyl-4-(2,2,2-trifluoroethoxy)-2-pyridyl]methyl]sulfinyl]-1H-benzimidazol-1-yl]carbonyl]amino]ethyl acetate;
ethyl 2-[isopropyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate;
2-[cyclohexyl[[(R)-2-[[[3-methyl-4-(2,2,2-trifluoroethoxy)-2-pyridyl]methyl]sulfinyl]-1H-benzimidazol-1-yl]carbonyl]amino]ethyl acetate;
2-[cyclohexyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate;
2-[[[(R)-2-[[[3-methyl-4-(2,2,2-trifluoroethoxy)-2-pyridyl]methyl]sulfinyl]-1H-benzimidazol-1-yl]carbonyl](phenyl)amino]ethyl acetate;
2-[[[2-[[[3-methyl-4-(2,2,2-trifluoroethoxy)-2-pyridyl]methyl]sulfinyl]-1H-benzimidazol-1-yl]carbonyl](phenyl)amino]ethyl acetate;
tert-butyl [2-[methyl[[(R)-2-[[[3-methyl-4-(2,2,2-trifluoroethoxy)-2-pyridyl]methyl]sulfinyl]-1H-benzimidazol-1-yl]carbonyl]amino]-3-pyridyl]methyl carbonate;
2-[methyl[[(R)-2-[[[3-methyl-4-(2,2,2-trifluoroethoxy)-2-pyridyl]methyl]sulfinyl]-1H-benzimidazol-1-yl]carbonyl]amino]benzyl acetate;
2-[[2-(acetyloxy)ethyl][[(R)-2-[[[3-methyl-4-(2,2,2-trifluoroethoxy)-2-pyridyl)]methyl]sulfinyl]-1H-benzimidazol-1-yl]carbonyl]amino]ethyl acetate;
[(2S)-1-[[(R)-2-[[[3-methyl-4-(2,2,2-trifluoroethoxy)-2-pyridyl]methyl]sulfinyl]-1H-benzimidazol-1-yl]carbonyl]-2-pyrrolidinyl]methyl acetate;
ethyl [methyl[[(R)-2-[[[3-methyl-4-(2,2,2-trifluoroethoxy)-2-pyridyl]methyl]sulfinyl]-1H-benzimidazol-1-yl]carbonyl]amino]acetate;
2-[[[5-methoxy-2-[[(4-methoxy-3,5-dimethyl-2-pyridyl)methyl]sulfinyl]-1H-benzimidazol-1-yl]carbonyl](methyl)amino]ethyl benzoate;
3-[methyl[[(R)-2-[[[3-methyl-4-(2,2,2-trifluoroethoxy)-2-pyridyl]methyl]sulfinyl]-1H-benzimidazol-1-yl]carbonyl]amino]propyl benzoate;
2-[methyl[[2-[[[3-methyl-4-(2,2,2-trifluoroethoxy)-2-pyridyl]methyl]sulfinyl]-1H-benzimidazol-1-yl]carbonyl]amino]ethyl tetrahydropyran-4-yl carbonate;
ethyl 2-[methyl[[2-[[[3-methyl-4-(2,2,2-trifluoroethoxy)-2-pyridyl]methyl]sulfinyl]-1H-benzimidazol-1-yl]carbonyl]amino]ethyl carbonate;
ethyl 2-[methyl[[(S)-2-[[[3-methyl-4-(2,2,2-trifluoroethoxy)-2-pyridyl]methyl]sulfinyl]-1H-benzimidazol-1-yl]carbonyl]amino]ethyl carbonate;
ethyl 2-[[[(5-methoxy-2-[[(4-methoxy-3,5-dimethyl-2-pyridyl)methyl]sulfinyl]-3H-imidazo[4,5-b]pyzidin-3-yl]carbonyl](methyl)amino]ethyl carbonate;
2-[[[5-methoxy-2-[[(4-methoxy-3,5-dimethyl-2-pyridyl)methyl]sulfinyl]-3H-imidazo[4,5-b]pyzidin-3-yl]carbonyl](methyl)amino]ethyl acetate;
2-[[[5-methoxy-2-[[(4-methoxy-3,5-dimethyl-2-pyridyl)methyl]sulfinyl]-3H-imidazo[4,5-b]pyridin-3-yl]carbonyl](phenyl)amino]ethyl acetate;
4-[methyl[[(R)-2-[[[3-methyl-4-(2,2,2-trifluoroethoxy)-2-pyridyl]methyl]sulfinyl]-1H-benzimidazol-1-yl]carbonyl]amino]butyl acetate;
ethyl 4-[methyl[[(R)-2-[[[3-methyl-4-(2,2,2-trifluoroethoxy)-2-pyridyl]methyl]sulfinyl]-1H-benzimidazol-1-yl]carbonyl]amino]butyl carbonate;
ethyl 3-[methyl[[(R)-2-[[[3-methyl-4-(2,2,2-trifluoroethoxy)-2-pyridyl]methyl]sulfinyl]-1H-benzimidazol-1-yl]carbonyl]amino]propyl carbonate;
3-[methyl[[(R)-2-[[[3-methyl-4-(2,2,2-trifluoroethoxy)-2-pyridyl]methyl]sulfinyl]-1H-benzimidazol-1-yl]carbonyl]amino]propyl acetate;
3-[methyl[[(r)-2-[[[3-methyl-4-(2,2,2-trifluoroethoxy)-2-pyridyl]methyl]sulfinyl]-1H-benzimidazol-1-yl]carbonyl]amino]propane-1,2-diyl diacetate;
diethyl 3-[methyl[[(R)-2-[[[3-methyl-4-(2,2,2-trifluoroethoxy)-2-pyridyl]methyl]sulfinyl]-1H-benzimidazol-1-yl]carbonyl]amino]propane-1,2-diyl biscarbonate;

2-[[[5-methoxy-2-[[(4-methoxy-3,5-dimethyl-2-pyridyl)methyl]sulfinyl]-3H-imidazo[4,5-b]pyridin-3-yl]carbonyl](methyl)amino]ethyl 3-chlorobenzoate;
2-[methyl[[2-[[[3-methyl-4-(2,2,2-trifluoroethoxy)-2-pyridyl]methyl]sulfinyl]-1H-benzimidazol-1-yl]carbonyl]amino]ethyl acetate;
2-ethoxyethyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate;
3-methoxypropyl 2-[methyl[[(R)-2-[[[3-methyl-4-(2,2,2-trifluoroethoxy)-2-pyridyl]methyl]sulfinyl]-1H-benzimidazol-1-yl]carbonyl)amino]ethyl carbonate;
2-[methyl([(R)-2-[[[3-methyl-4-(2,2,2-trifluoroethoxy)-2-pyridyl]methyl]sulfinyl]-1H-benzimidazol-1-yl]carbonyl]amino]ethyl N,N-dimethylglycinate;
S-[2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl]thioacetate;
ethyl 2-[2-[methyl[[(R)-2-[[[3-methyl-4-(2,2,2-trifluoroethoxy)-2-pyridyl]methyl]sulfinyl]-1H-benzimidazol-1-yl]carbonyl]amino]ethoxy]ethyl carbonate;
ethyl 2-[methyl[[2-[methyl[[(R)-2-[[[3-methyl-4-(2,2,2-trifluoroethoxy)-2-pyridyl]methyl]sulfinyl]-1H-benzimidazol-1-yl]carbonyl]amino]ethoxy]carbonyl]-amino]ethyl carbonate;
ethyl 2-[[[5-methoxy-2-[[(4-methoxy-3,5-dimethyl-2-pyridyl)methyl]sulfinyl]-1H-benzimidazol-1-yl]carbonyl](methyl)amino]ethyl carbonate;
2-[[[5-methoxy-2-[[4-methoxy-3,5-dimethyl-2-pyridyl)methyl]sulfinyl]-1H-benzimidazol-1-yl]carbonyl](phenyl)amino]ethyl acetate;
ethyl 2-[[[(S)-5-methoxy-2-[[(4-methoxy-3,5-dimethyl-2-pyridyl)methyl]sulfinyl]-1H-benzimidazol-1-yl]carbonyl](methyl)amino]ethyl carbonate;
ethyl 2-[[[2-[[[4-(3-methoxypropoxy)-3-methyl-2-pyridyl]methyl]sulfinyl]-1H-benzimidazol-1-yl]carbonyl](methyl)amino]ethyl carbonate;
2-[[[2-[[[4-(3-methoxypropoxy)-3-methyl-2-pyridyl]methyl]sulfinyl]-1H-benzimidazol-1-yl]carbonyl](phenyl)amino]ethyl acetate;
2-[[[5-(difluoromethoxy)-2-[[(3,4-dimethoxy-2-pyridyl)methyl]sulfinyl]-1H-benzimidazol-1-yl]carbonyl](methyl)amino]ethyl carbonate;
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl 1-methylpiperidine-4-carboxylate;
2-[[4-(aminocarbonyl)phenyl][[(R)-2-[[[3-methyl-4-(2,2,2-trifluoroethoxy)-2-pyridyl]methyl]sulfinyl]-1H-benzimidazol-1-yl]carbonyl]amino]ethyl acetate;
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl 1-methyl-4-piperidinyl carbonate;
2-[[4-(aminocarbonyl)phenyl][[2-[[[3-methyl-4-(2,2,2-trifluoroethoxy)-2-pyridyl]methyl]sulfinyl]-1H-benzimidazol-1-yl]carbonyl]amino]ethyl acetate;
(−)-ethyl 2-[[[5-methoxy-2-[[(4-methoxy-3,5-dimethyl-2-pyridyl)methyl]sulfinyl]-3H-imidazo[4,5-b]pyridin-3-yl]carbonyl(methyl)amino]ethyl carbonate; and
(+)-ethyl 2-[[[5-methoxy-2-[[(4-methoxy-3,5-dimethyl-2-pyridyl)methyl]sulfinyl]-3H-imidazo[4,5-b]pyridin-3-yl]carbonyl(methyl)amino]ethyl carbonate; and salts thereof.
The following compounds and salts thereof are particularly preferable:
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl acetate;
ethyl 2-[methyl[[(R)-2-[[[3-methyl-4-(2,2,2-trifluoroethoxy)-2-pyridyl]ethyl]sulfinyl]-1H-benzimidazol-1-yl]carbonyl]amino]ethyl carbonate;
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl tetrahydropyran-4-yl carbonate;
2-[methyl[[2-[[[3-methyl-4-(2,2,2-trifluoroethoxy)-2-pyridyl]methyl]sulfinyl]-1H-benzimidazol-1-yl]carbonyl]amino]ethyl tetrahydropyran-4-yl carbonate;
ethyl 2-[methyl[[2-[[[3-methyl-4-(2,2,2-trifluoroethoxy)-2-pyridyl]methyl]sulfinyl]-1H-benzimidazol-1-yl]carbonyl]amino]ethyl carbonate;
ethyl 2-[[[5-methoxy-2-[[(4-methoxy-3,5-dimethyl-2-pyridyl)methyl]sulfinyl]-3H-imidazo[4,5-b]pyridin-3-yl]carbonyl](methyl)amino]ethyl carbonate;
2-[[[5-methoxy-2-[[(4-methoxy-3,5-dimethyl-2-pyridyl)methyl]sulfinyl]-3H-imidazo[4,5-b]pyridine-3-yl]carbonyl](methyl)amino]ethyl acetate;
2-[methyl[[2-[[[3-methyl-4-(2,2,2-trifluoroethoxy)-2-pyridyl]methyl]sulfinyl]-1H-benzimidazol-1-yl]carbonyl]amino]ethyl acetate;
ethyl 2-[[[5-methoxy-2-[[(4-methoxy-3,5-dimethyl-pyridyl)methyl]sulfinyl]-1H-benzimidazol-1-yl]carbonyl](methyl)amino]ethyl carbonate;
ethyl 2-[[[(S)-5-methoxy-2-[[(4-methoxy-3,5-dimethyl-2-pyridyl)methyl]sulfinyl]-1H-benzimidazol-1-yl]carbonyl](methyl)amino]ethyl carbonate;
ethyl 2-[[[2-[[[4-(3-methoxypropoxy)-3-methyl-2-pyridyl]methyl]sulfinyl]-1H-benzimidazol-1-yl]carbonyl](methyl)amino]ethyl carbonate; and
2-[[[5-(difluoromethoxy)-2-[[(3,4-dimethoxy-2-pyridyl)methyl]sulfinyl]-1H-benzimidazol-1-yl]carbonyl](methyl)amino]ethyl carbonate.

The compound (II) can be produced according to JP-A 2004-307457.

Examples of the above-described prodrug include a benzimidazole compound represented by the following formula (III):

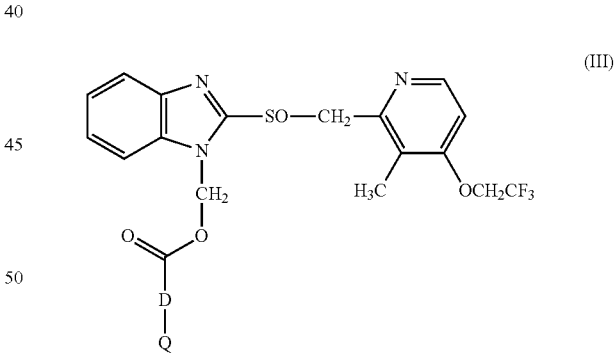

and a salt thereof.

In the formula (III), D represents an oxygen atom or a bond, and Q represents a optionally substituted hydrocarbon group.

The "hydrocarbon group" of the "optionally substituted hydrocarbon group" represented by Q includes an aliphatic hydrocarbon group and an aromatic hydrocarbon group. The aliphatic hydrocarbon group as used herein refers to a saturated or unsaturated, linear, branched or cyclic hydrocarbon group. The hydrocarbon group has preferably 1 to 14 carbon atoms, and examples thereof include $C_{1-6}$ alkyl, ($C_{2-6}$ alkenyl, $C_{2-6}$ alkynyl, $C_{3-8}$ cycloalkyl and $C_{6-14}$ aryl groups, preferably $C_{1-6}$ alkyl, $C_{3-8}$ cycloalkyl and $C_{6-14}$ aryl groups, and more preferably $C_{1-6}$ alkyl and $C_{3-8}$ cycloalkyl groups.

The "alkyl group" refers to a linear or branched alkyl group, preferably an alkyl group having 1 to 6 carbon atoms ("$C_{1-6}$ alkyl group"). Examples of the alkyl group include methyl, ethyl, n-propyl, isopropyl, n-butyl, isobutyl, sec-butyl, tert-butyl, n-pentyl, isopentyl, neopentyl, 1-methylpropyl, n-hexyl, isohexyl, 1,1-dimethylbutyl, 2,2-dimethylbutyl, 3,3-dimethylbutyl, 3,3-dimethylpropyl and 2-ethylbutyl. More preferred are alkyl groups having 1 to 4 carbon atoms. Examples of the "alkyl group" represented by Q include preferably methyl, ethyl, isopropyl and tert-butyl, and more preferably tert-butyl.

The "$C_{2-6}$ alkenyl group" refers to a linear or branched alkenyl group having 2 to 6 carbon atoms, and examples of the alkenyl group include vinyl, n-propenyl, isopropenyl, n-butenyl, isobutenyl, sec-butenyl, tert-butenyl, n-pentenyl, isopentenyl, neopentenyl, 1-methylpropenyl, n-hexenyl, isohexenyl, 1,1-dimethylbutenyl, 2,2-dimethylbutenyl, 3,3-dimethylbutenyl, 3,3-dimetylpropenyl and 2-ethylbutenyl. Preferred are alkenyl groups having 2 to 4 carbon atoms, inter alia, vinyl, n-propenyl and isopropenyl.

The "$C_{2-6}$ alkynyl group" refers to a linear or branched alkynyl group having 2 to 6 carbon atoms. Examples of the alkynyl group include ethynyl, n-propynyl(1-propynyl), isopropynyl (2-propynyl), n-butynyl, isobutynyl, sec-butynyl, tert-butynyl, n-pentynyl, isopentynyl, neopentynyl, 1-methylpropynyl, n-hexynyl, isohexynyl, 1,1-dimethylbutynyl, 2,2-dimethylbutynyl, 3,3-dimethylbutynyl, 3,3-dimethylpropynyl and 2-ethylbutynyl. Preferred are alkynyl groups having 2 to 3 carbon atoms, inter alia, ethynyl, 1-propynyl and 2-propynyl.

The "$C_{3-6}$ cycloalkyl group" refers to a linear or branched cycloalkyl group having 3 to 8 carbon atoms. Examples of the cycloalkyl group include cyclopropyl, cyclobutyl, cyclopentyl, cyclohexyl, cycloheptyl and cyclooctyl. Preferred are cycloalkyl groups having 5 to 7 carbon atoms, inter alia, cyclopentyl, cyclohexyl and cycloheptyl, and particularly cyclohexyl.

The "aryl group" refers to a monocyclic or fused polycyclic aromatic hydrocarbon group, preferably an aromatic hydrocarbon group having 6 to 14 carbon atom ("$C_{6-14}$ aryl group"). Examples of the aryl group include phenyl, naphthyl, anthryl, phenanthryl and acenaphthylenyl. Preferred are aromatic hydrocarbon groups having 6 to 10 carbon atoms. Among them, a particularly preferable example of the "aryl group" represented by Q is phenyl.

The "hydrocarbon group" may be substituted, and examples of the substituent include $C_{6-14}$ aryl, hydroxyl, halogen, $C_{1-6}$ alkoxy that may be substituted with halogen, $C_{7-12}$ aralkyloxy, $C_{1-6}$ alkoxy-carbonyl, $C_{1-6}$ alkyl that may be substituted with halogen, and amino that may be substituted with $C_{1-6}$ alkyl.

Examples of the substituent for the "optionally substituted alkyl group" include aryl, hydroxyl, halogen, alkoxy that may be substituted with 1 to 5 halogen, $C_{7-12}$ aralkyloxy and $C_{1-6}$ alkoxy-carbonyl. The number of the substituent is 1 to 5, preferably 1 to 3.

Examples of the substituent for the "optionally substituted aryl group" include halogen, alkyl that may be substituted with 1 to 5 halogen, aryl, hydroxyl, alkoxy that may be substituted with 1 to 5 halogen, $C_{7-12}$ aralkyloxy, and $C_{1-5}$ alkoxy-carbonyl. The number of substituent is 1 to 5, preferably 1 to 3.

The "$C_{1-6}$ alkyl group", "$C_{2-6}$ alkenyl group" and "$C_{2-6}$ alkynyl group" may be substituted. Examples of the substituent include (i) $C_{6-14}$ aryl, (ii) hydroxyl, (iii) halogen, (iv) $C_{1-6}$ alkoxy that may be substituted with halogen, (v) $C_{7-12}$ aralkyloxy, (vi) $C_{1-6}$ alkoxy-carbonyl, (vii) acylamino, and (viii) amino that may be substituted with $C_{1-6}$ alkyl, inter alia, preferably (i) to (vii). The number of the substituent is 1 to 5, preferably 1 to 3.

The "$C_{3-8}$ cycloalkyl group" and "$C_{6-14}$ aryl group" may be substituted. Examples of the substituent include (i) $C_{6-14}$ aryl, (ii) hydroxyl, (iii) halogen, (iv) $C_{1-6}$ alkoxy that may be substituted with halogen, (v) $C_{7-12}$ aralkyloxy, (vi) $C_{1-6}$ alkoxy-carbonyl, (vii) $C_{1-6}$ alkyl that may be substituted with halogen, and (viii) amino that may be substituted with $C_{1-6}$ alkyl, inter alia, preferably (i) to (vii). The number of the substituent is 1 to 5, preferably 1 to 3.

In the formula (III), Q is preferably a $C_{1-6}$ alkyl group, a $C_{2-6}$ alkenyl group or a $C_{2-6}$ alkynyl group that may have substituent(s) selected from the group consisting of (i) $C_{6-14}$ aryl, (ii) hydroxyl, (iii) halogen, (iv) $C_{1-6}$ alkoxy that may be substituted with halogen, (v) $C_{7-12}$ aralkyloxy, (vi) $C_{1-6}$ alkoxy-carbonyl and (vii) acylamino; or a $C_{3-8}$ cycloalkyl group or a $C_{6-14}$ aryl group that may have substituent(s) selected from the group consisting of (i) $C_{6-14}$ aryl, (ii) hydroxyl, (iii) halogen, (iv) $C_{1-6}$ alkoxy that may be substituted with halogen, (v) $C_{7-12}$ aralkyloxy, (vi) $C_{1-6}$ alkoxy-carbonyl, and (vii) $C_{1-6}$ alkyl that may be substituted with halogen;

more preferably (1) a $C_{1-6}$ alkyl group that may have 1 to 5 substituents selected from the group consisting of (i) $C_{6-14}$ aryl, (ii) hydroxyl, (iii) halogen, (iv) $C_{1-6}$ alkoxy that may be substituted with 1 to 5 halogen, (v) $C_{7-12}$ aralkyloxy and (vi) $C_{1-6}$ alkoxy-carbonyl; or (2) a $C_{6-14}$ aryl group that may have 1 to 5 substituents selected from the group consisting of (i) halogen, (ii) $C_{1-6}$ alkyl that may be substituted with 1 to 5 halogen, (iii) $C_{6-14}$ aryl, (iv) hydroxyl, (v) $C_{1-6}$ alkoxy that may be substituted with 1 to 5 halogen, (vi) $C_{7-12}$ aralkyloxy and (vii) $C_{1-6}$ alkoxy-carbonyl; and further preferably a $C_{1-6}$ alkyl group that may have substituent(s) selected from the group consisting of (i) $C_{6-14}$ aryl, (ii) hydroxyl, (iii) halogen, (iv) $C_{1-6}$ alkoxy that may be substituted with halogen, (v) $C_{7-12}$ aralkyloxy, (vi) $C_{1-6}$ alkoxy-carbonyl and (vii) acylamino; or a $C_{3-8}$ cycloalkyl group or a $C_{6-14}$ aryl group that may have substituent(s) selected from the group consisting of (i) $C_{6-14}$ aryl, (ii) hydroxyl, (iii) halogen, (iv) $C_{1-6}$ alkoxy that may be substituted with halogen, (v) $C_{7-12}$ aralkyloxy, (vi) $C_{1-6}$ alkoxy-carbonyl and (vii) $C_{1-6}$ alkyl that may be substituted with halogen.

Among them, Q is preferably a $C_{1-6}$ alkyl group or a $C_{6-14}$ aryl group that may be substituted with $C_{6-14}$ aryl, and particularly preferably a phenyl group, a methyl group or a tert-butyl group.

The compound (III) can form a pharmacologically acceptable base salt via an acidic group in the molecule with an inorganic or organic base or the like, or a pharmacologically acceptable acid addition salt via a basic group in the molecule with an inorganic or organic acid or the like.

In a suitable aspect of the compound (III) of the present invention, D is a bond, and Q is an optionally substituted alkyl group or an optionally substituted aryl group.

Examples of the inorganic base salt of the compound (III) include salts with alkali metals (for example, sodium, potassium, and the like), alkali earth metals (for example, calcium, and the like), ammonia and the like. Examples of the organic base salt of the compound (III) include salts with dimethylamine, triethylamine, piperazine, pyrrolidine, piper idine, 2-phenylethylamine, benzylamine, ethanolamine, diethanolamine, pyridine, collidine, and the like.

Examples of the acid addition salt of the compound (III) include inorganic acid salts (for example, hydrochloride, sulfate, hydrobromate, phosphate, and the like) and organic acid salts (for example, acetate, trifluoroacetate, succinate, maleate, fumarate, propionate, citrate, tartrate, lactate, oxalate, methanesulfonate, p-toluenesulfonate, and the like).

The compound (III) of the present invention may be a hydrate. Examples of the "hydrate" include 0.5 to 5.0 hydrates, and preferred are a 0.5 hydrate, a 1.0 hydrate, a 1.5 hydrate and a 2.0 hydrate.

The compound (III) of the present invention includes racemates and optically active compounds. The optically active compound has an enantiomeric excess (e.e.) of preferably 90% or more, more preferably 99 or more based on one of the enantiomers. The optically active compound is preferably (R)-isomer represented by the following formula:

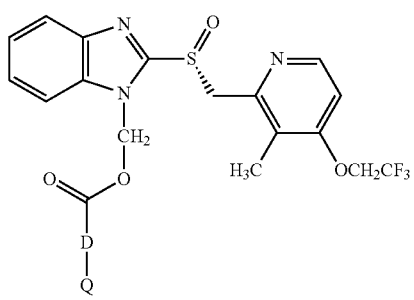

wherein symbols are as defined above.

The compound (III) can be produced by a per se known method, for example, a method described in JP-A 2002-187890 or in WO 02/030920 or a similar methods thereto. The optically active compound (III) can be obtained by an optical resolution method (a fractional recrystallization method, a chiral column method, a diastereomer method or a method using an enzyme or a microbe), asymmetric oxidation or the like. The compound described in WO 03/27098 as PPI of other benzimidazole derivatives can be also used as the biologically active substance of the present invention.

The amount of the biologically active substance used in the present invention differs depending on the kind of the biologically active substance and dosage, and for example, it is about 1% by weight to about 60% by weight, preferably about 1% by weight to about 50% by weight, and more preferably about 8% by weight to about 40% by weight of the total granule amount of the present invention. When the biologically active substance is PPI such as a benzimidazole compound, particularly lansoprazole or an optically active compound thereof, the amount used of the biologically active substance is about 8% by weight to about 40% by weight.

Since a biologically active substance having low toxicity is used for production of the granules of the present invention, the obtained granules can be safely and orally administered as they are or as a pharmaceutical composition such as tablet, capsule or intraorally disintegrating tablet which is produced by mixing and molding together with a pharmacologically acceptable carrier according to a per se known method.

A daily dose of the granule produced by the method of the present invention varies depending on severity of symptoms, the age, sexuality and body weight of a recipient, timing and interval of administration, the kind of an active ingredient, and the like, and is not particularly limited. For example, the granule is orally administered in an amount of about 0.5 to 1500 mg/day, preferably about 5 to 150 mg/day of an active ingredient, to an adult (body weight 60 kg) as an antiulcer drug or the like. The preparation may be administered once a day or in 2 to 3 divided doses a day.

Since a benzimidazole compound used in the present invention (for example lansoprazole or an optically active compound thereof, or pharmaceutically acceptable salts thereof), in particular (R)-lansoprazole, exhibits a proton pump inhibitory effect and effectively suppresses the secretion of gastric acid, it is useful for treatment and prophylaxis of peptic ulcers (for example gastric ulcer, gastric ulcer due to postoperative stress, duodenal ulcer, anastomotic ulcer, ulcer caused by a non-steroidal anti-inflammatory drug, and the like); gastritis; erosive and non-erosive esophagitis; reflux esophagitis such as erosive and non-errosive reflux esophagitis; symptomatic gastroesophageal reflux disease (Symptomatic GERD) such as erosive and non-erosive gastroesophageal reflux disease; NUD (Non Ulcer Dyspepsia); gastric cancer (including gastric cancer accompanied by enhanced production of interleukin-1β due to genetic polymorphism of interleukin-1); gastric MALT lymphoma; Zollinger-Ellison syndrome; hyperchlorhydria (for example hyperchlorhydria and an ulcer due to postoperative stress); upper digestive tract hemorrhage caused by peptic ulcers, acute stress ulcers, hemorrhagic gastritis or invasive stress (stress caused by cerebrovascular accident, head trauma, multiple organ failure or extensive burn which needs a major operation requiring centralized control after the operation or intensive care), for administration before anesthesia, for removal and assistance of removal of *Helicobacter pylori*, and the like, in mammals (such as human, monkey, sheep, cattle, horse, dog, cat, rabbit, rat, mouse, and the like).

Herein, reflux esophagitis and symptomatic gastroesophageal reflux disease (Symptomatic GERD) may be collectively referred to as GEPD.

Hereinafter, the present invention is described in more detail with reference to Examples and Experimental examples to which the present invention is not limited.

Corn starch, hydroxypropyl cellulose (HPC-L), polyethyleneglycol 6000 and titanium oxide used in Examples of pharmaceutical preparations were in conformity with Japanese pharmacopoeia (14th edition).

Example 1

Composition is shown in Table 1. (R)-Lansoprazole (7,290 g), magnesium carbonate (1,944 g), sucrose (roughly ground, 4,820 g) and low substituted hydroxypropyl cellulose (1,458 g) were mixed using a vertical granulator to prepare a spraying or dusting material containing an active pharmaceutical ingredient (15,494 g in total). Sucrose-corn starch spherical granules (4,500 g; NONPAREIL 101-750, manufactured by Freund Co.) were put in a centrifugal fluidized bed granulator (CF-600S, manufactured by Freund Co.) as cores, and then sprayed or dusted with the spraying or dusting material containing an active pharmaceutical ingredient (14,346 g) while being sprayed with a solution of hydroxypropyl cellulose (2% aqueous solution: W/W) (final spray amount: 54 g (solid matter)) to obtain spherical granules. The coating was performed under the conditions of rotor speed: 160 rpm, linear velocity: 339 m/mm, and spraying or dusting speed of the active pharmaceutical ingredient per 1 g of the core: 78 mg/min/g. The spherical granules obtained were dried under vacuum at 40° C. for 16 hours, and sieved with a round sieve to obtain active pharmaceutical ingredient granules A with a particle size of 710 μm to 1400 μm.

The active pharmaceutical ingredient granules A thus obtained (15,120 g) were coated with an intermediate layer coating liquid (19,860 g, solid content: 1.0%) using a fluidized bed granulation coating machine (FD-S2, manufactured by POWREX Co.). The coating was performed under the conditions of air supply rate: 7 m³/min, air supply temperature: 65° C. and product temperature: 40° C. (pre-heating temperature during the process). The spherical granules thus obtained were dried in vacuum at 40° C. for 16 hours, and then sieved with a round sieve to obtain intermediate layer granules A with a particle size of 710 µm to 1,400 µm.

The intermediate layer granules A thus obtained were heated at 70° C. for 5, 10 and 15 minutes to obtain intermediate layer granules A-5, A-10 and A-15 respectively.

TABLE 1

<Composition of Active Pharmaceutical Ingredient Granule (equivalent to 67.5 mg of (R)-Lansoprazole:)>
(Core)

| Sucrose-Starch Spherical Granule | 45 mg |
|---|---|
| (Spraying or Dusting Material Containing Active Pharmaceutical Ingredient) | |
| (R)-Lansoprazole | 67.5 mg |
| Magnesium Carbonate | 18 mg |
| Sucrose (ground) | 44.46 mg |
| Low Substituted Hydroxypropyl Cellulose | 13.5 mg |
| (Binder Liquid) | |
| Hydroxypropyl Cellulose | 0.54 mg |
| Purified Water | 26.46 mg |
| Total (Solid matter) | 189 mg |
| <Composition of Intermediate Layer Coating Liquid> | |
| Hydroxypropylmethyl Cellulose | 11.82 mg |
| Talc | 4.74 mg |
| Titanium Oxide | 7.08 mg |
| Purified Water | 212.76 mg |
| Total (Solid matter) | 23.58 mg |
| <Composition of Intermediate Layer Granule A> | |
| Active Pharmaceutical Ingredient Granule A | 189.0 mg |
| Intermediate Layer Coating Liquid | 23.58 mg |
| Total | 212.64 mg |

Experimental Example 1

The intermediate layer granules A, A-5, A-10 and A-15 obtained in Example 1 were tested for dissolution property in a phosphate buffer (pH 6.8). Table 2 shows the proportion of the amount of an active ingredient dissolved after 20 minutes to the total amount (content) of the active ingredient contained in the intermediate layer granule, that is, dissolution rate (%).

TABLE 2

| Time | Dissolution rate (%) | | | |
|---|---|---|---|---|
| (minutes) | A | A-5 | A-10 | A-15 |
| 20 | 68.3 | 100.2 | 97.2 | 103.4 |

While the intermediate layer granule A, which was untreated, showed a dissolution rate after 20 minutes of about 70%, all the intermediate layer granules A-5, A-10 and A-15, which were subjected to heat treatment, showed a dissolution rate of almost 100%.

Example 2

Composition is shown in Table 3. The intermediate layer granules A obtained in Example 1 were put in a fluidized bed granulation coating machine (MP-10, manufactured by POWREX Co.) and then heated at 70° C. for 5 minutes. Subsequently, the granules were coated with a coating liquid for forming a pH-dependent soluble controlled-release film. The spherical granules thus obtained were dried in vacuum at 40° C. for 16 hours and sieved with a round sieve to obtain pH-dependent soluble controlled-release granules A with a particle size of 1,000 µm to 1,700 µm.

TABLE 3

<Composition of Coating Liquid for pH-Dependent Soluble Controlled-Release Coating Film>

| Methacrylic Acid Copolymer (Type B) | 47.85 mg |
|---|---|
| Methacrylic Acid Copolymer (Type A) | 15.96 mg |
| Triethyl Citrate | 6.36 mg |
| Talc | 31.89 mg |
| Ethanol | 826.69 mg |
| Purified Water | 91.85 mg |
| Total (Solid matter) | 102.06 mg |
| <Composition of pH-Dependent Soluble Controlled-Release Granule A> | |
| Intermediate: Layer Granule A | 212.64 mg |
| Coating Liquid for pH-Dependent Soluble Controlled-Release Coating Film | 102.06 mg |
| Total | 314.7 mg |

Example 3

Composition is shown in Table 4. (R)-Lansoprazole (3,645 g), magnesium carbonate (972 g), sucrose (ground, 2,401 g) and low substituted hydroxypropyl cellulose (729 g) were mixed using a vertical granulator to prepare a spraying or dusting material containing an active pharmaceutical ingredient (7,747 g in total). Sucrose-corn starch spherical granules (2,250 g; NONPAREIL 101-750, manufactured by Freund Co.) were put in a centrifugal fluidized bed granulator (CF-600S, manufactured by Freund Co.) as cores, and then sprayed or dusted with the spraying or dusting material containing an active pharmaceutical ingredient (7,173 g) while being sprayed with a solution of hydroxypropyl cellulose (2% aqueous solution: W/W) (final spraying amount: 27 g (solid matter)) to obtain spherical granules. The coating was performed under the conditions of rotor speed: 120 rpm, linear velocity: 226 m/min, and spraying or dusting speed of the active pharmaceutical ingredient per 1 g of the core: 147 mg/min/g. The spherical granules obtained were dried in vacuum at 40° C. for 16 hours, and sieved with a round sieve to obtain active pharmaceutical ingredient granules B with a particle size of 710 µm to 1,400 µm.

The active pharmaceutical ingredient granules B thus obtained (15,120 g) were coated with an intermediate layer coating liquid (19,860 g, solid content: 10%) using a fluidized bed granulation coating machine (FD-S2, manufactured by POWREX Co.). The coating was performed under the conditions of air supply rate: 7 m³/min, air supply temperature: 65° C. and product temperature: 40° C. (pre-heating temperature during the process). The spherical granules thus obtained were dried in vacuum at 40° C. for 16 hours, and sieved with a round sieve to obtain intermediate layer granules B with a particle size of 710 µm to 1,400 µm.

The intermediate layer granules B thus obtained (18,070 q) were put in a fluidized bed granulation coating machine (FD-82, manufactured by POWREX Co.) and then heated at 70° C. for 5 minutes. Subsequently, the granules were coated with an enteric film coating liquid (23,850 g; solid content: 18%). The coating was performed under the conditions of air supply rate:

1.5 m³/min, air supply temperature: 65° C., liquid injection speed: 15 g/min and air spray pressure: 3 kg/cm². The spherical granules thus obtained were dried in vacuum at 40° C. for 16 hours, and sieved with a round sieve to obtain enteric granules A with a particle size of 850 µm to 1,400 µm.

The intermediate layer granules B (15,310 g) obtained as described above were put in a fluidized bed granulation coating machine (FD-S2, manufactured by POWREX Co.), and then heated at 70° C. for 5 minutes. Subsequently, the granules were coated with a coating liquid (77,160 g, solid content: 10%) for forming a pH-dependent soluble controlled-release coating film. The spherical granules thus obtained were dried in vacuum at 40° C. for 16 hours, and sieved with a round sieve to obtain pH-dependent soluble controlled-release granules B with a particle size of 1,000 µm to 1,700 µm.

Talc and colloidal silicon dioxide were mixed with the enteric granules A or the pH-dependent soluble controlled-release granules B. Both of the enteric mixed granules A thus obtained (87 mg: equivalent to 22.5 mg of (R)-lansoprazole) and the pH-dependent soluble controlled-release mixed granules B thus obtained (315 mg: equivalent to 67.5 mg of (R)-lansoprazole) were encapsulated into a No. 1 long HPMC capsule.

The HPMC capsule thus obtained was dried in vacuum at 40° C. for 2 hours to obtain an HPMC Capsule preparation with a moisture content of 22% ERH or less.

TABLE 4

Composition Table

| | Enteric Mixed Granule A | pH-dependent Soluble Controlled-Release Mixed Granule B |
|---|---|---|
| <Composition of Active Pharmaceutical Ingredient Granule> | | |
| Sucrose-Starch Spherical Granule | 15.0 mg | 45.0 mg |
| (Spraying or Dusting Material Containing Active Pharmaceutical Ingredient) | | |
| (R)-Lansoprazole | 22.5 mg | 67.5 mg |
| Magnesium Carbonate | 6.0 mg | 18.0 mg |
| Sucrose (ground) | 14.82 mg | 44.46 mg |
| Low Substituted Hydroxypropyl Cellulose | 4.5 mg | 13.5 mg |
| (Binder Liquid) | | |
| Hydroxypropyl Cellulose | 0.18 mg | 0.54 mg |
| Purified Water | 8.82 mg | 26.46 mg |
| Total (Solid matter) | 63.0 mg | 189.0 mg |
| <Composition of Intermediate Layer Coating Liquid> | | |
| Hydroxypropylmethyl cellulose | 3.94 mg | 11.82 mg |
| Talc | 1.58 mg | 4.74 mg |
| Titanium Oxide | 2.36 mg | 7.08 mg |
| Purified water | 70.92 mg | 212.76 mg |
| Total (Solid matter) | 7.86 mg | 23.58 mg |
| <Composition of Intermediate Layer Granule B> | | |
| Active Pharmaceutical Ingredient Granule B | 63.0 mg | 189.0 mg |
| Intermediate Layer Coating Liquid | 7.86 mg | 23.58 mg |
| Total | 70.88 mg | 212.64 mg |
| <Composition of Coating Liquid for Enteric Coating Film> | | |
| Methacrylic Acid Copolymer (Dispersion Liquid) | 35.1 mg (Solid matter 10.53 mg) | — |
| Polyethyleneglycol 6000 | 1.05 mg | — |
| Polysorbate 80 | 0.48 mg | — |
| Titanium Oxide | 1.05 mg | — |
| Talc | 2.92 mg | — |
| Purified Water | 48.46 mg | — |
| Total (Solid matter) | 16.03 mg | — |
| <Composition of Enteric Granule> | | |
| Intermediate Layer Granule B | 70.88 mg | — |
| Coating Liquid for Enteric Coating Film | 16.03 mg | — |
| Total | 86.91 mg | — |
| <Composition of Coating Liquid for pH-Dependent Soluble Controlled-Release Coating Film> | | |
| Methacrylic Acid Copolymer (Type B) | — | 47.85 mg |
| Methacrylic Acid Copolymer (Type A) | — | 15.96 mg |
| Triethyl Citrate | — | 6.36 mg |
| Talc | — | 31.89 mg |
| Ethanol | — | 826.69 mg |
| Purified Water | — | 91.85 mg |
| Total (Solid matter) | — | 102.06 mg |
| <Composition of pH-dependent Solubles Controlled-Release Granule> | | |
| Intermediate Layer Granule B | — | 212.64 mg |
| Coating Liquid for pH-dependent Soluble Controlled-Release Coating Film | — | 102.06 mg |
| Total | — | 314.7 mg |
| <Composition of Enteric Mixed Granule and pH-Dependent Soluble Controlled-Release Mixed Granule> | | |
| Enteric Granule A | 86.91 mg | — |
| pH-Dependent Soluble Controlled-Release Granule B | — | 314.7 mg |
| Talc | 0.045 mg | 0.195 mg |
| Colloidal Silicon Dioxide | 0.045 mg | 0.195 mg |
| Total | 87.0 mg | 315.0 mg |

| | HPMC Capsule preparation |
|---|---|
| <Composition of Capsule Preparation (equivalent to 90 mg of (R)-Lansoprazole)> | |
| Enteric Mixed Granule A | 87.0 mg |
| pH-Dependant Soluble Controlled-Release Mixed Granule B | 315.0 mg |
| GPMC Capsule | No. 1 Long Capsule |

Example 4

Composition is shown in Table 5. (R)-Lansoprazole (3,645 g), magnesium carbonate (972 g), sucrose (2,400 g, ground) and low substituted hydroxypropyl cellulose (729 g) were mixed using a vertical granulator to prepare a spraying or dusting material containing an active pharmaceutical ingredient (7,746 g in total). Sucrose-corn starch spherical granules (2,250 g; NONPAREIL 101-750, manufactured by Freund Co.) were put in a centrifugal fluidized bed granulator (CF-600S, manufactured by Freund Co.) as cores, and then sprayed or dusted with the spraying or dusting material containing an active pharmaceutical ingredient (7,173 g) while being sprayed with a solution of hydroxypropyl cellulose (2% aqueous solution: W/W) (final spray amount: 21.6 g (solid matter)) to obtain spherical granules. The coating was performed under the conditions of rotor speed: 120 rpm, linear velocity: 226 m/min, and spraying or dusting speed of the active pharmaceutical ingredient per 1 g of the core: 147 mg/min/g. The spherical granules obtained were dried in vacuum at 40° C. for 16 hours, and sieved with a round sieve to obtain active pharmaceutical ingredient granules C with a particle size of 710 μm to 1,400 μm.

TABLE 5

<Composition of Active Pharmaceutical Ingredient Granule (Solid ingredients)>

| (Core) | |
|---|---|
| Sucrose-Starch Spherical Granule (Spraying or Dusting Material Containing Active Pharmaceutical Ingredient) | 23.8% |
| (R)-Lansoprazole | 35.7% |
| Magnesium Carbonate | 7.1% |
| Sucrose (ground) | 23.6% |
| Low Substituted Hydroxypropyl Cellulose (Binder Liquid) | 7.1% |
| Hydroxypropyl Cellulose | 0.3% |
| Total | 100% |

Example 5

Granules of an active pharmaceutical ingredient having the same composition as the active pharmaceutical ingredient granule produced in Example 4 were produced under different production conditions. (R)-Lansoprazole (1,355 g), magnesium carbonate (361 g), sucrose (893 g; ground) and low substituted hydroxypropyl cellulose (271 g) were mixed using a vertical granulator to prepare a spraying or dusting material containing an active pharmaceutical ingredient (2,880 g in total). Sucrose-corn starch spherical granules (752.8 g; NONPAREIL 101-750, manufactured by Freund Co.) as cores were put in a centrifugal fluidized bed granulating machine (CF360, manufactured by Freund Co.), and then sprayed or dusted with the spraying or dusting material containing an active pharmaceutical ingredient (2,400 g) while being sprayed with a solution of hydroxypropyl cellulose (2% aqueous solution: W/W) (final spray amount: 9 g (solid matter)) to obtain spherical granules. The coating was performed under the conditions of rotor speed: 240 rpm, linear velocity: 271 m/min, and spraying or dusting speed of the active pharmaceutical ingredient per 1 g of the core: 139 mg/min/g. The spherical granules obtained were dried in vacuum at 40° C. for 16 hours, and sieved with a round sieve to obtain active pharmaceutical ingredient granules D with a particle size of 710 μm to 1,400 μm.

Example 6

Composition is shown in Table 6. (R)-Lansoprazole (493 g), magnesium carbonate (361 g), sucrose (1,745 g; ground) and low substituted hydroxypropyl cellulose (272 g) were mixed using a vertical granulator to prepare a spraying or dusting material containing an active pharmaceutical ingredient (2,880 g in total). Sucrose-corn starch spherical granules (755.8 g; NONPAREIL 101-750, manufactured by Freund Co.) as cores were put in a centrifugal fluidized bed granulation machine (CF360, manufactured by Freund Co.), and then sprayed or dusted with the spraying or dusting material containing an active pharmaceutical ingredient (2,400 g) while being sprayed with a solution of hydroxypropyl cellulose (2% aqueous solution: W/W) (final spray amount: 8.8 g (solid matter)) to obtain spherical granules. The coating was performed under the conditions of rotor speed: 240 rpm, linear velocity: 271 m/min, and spraying or dusting speed of the active pharmaceutical ingredient per 1 g of the core: 139 mg/min/g. The spherical granules obtained were dried in vacuum at 40° C. for 16 hours, and sieved with a round sieve to obtain active pharmaceutical ingredient granules E with a particle size of 710 μm to 1,400 μm.

TABLE 6

<Composition of Active Pharmaceutical Ingredient Granule (Solid ingredients)>

| (Core) | |
|---|---|
| Sucrose-Starch Spherical Granule (Spraying or Dusting Material Containing Active Pharmaceutical Ingredient) | 23.9% |
| (R)-Lansoprazole | 13% |
| Magnesium Carbonate | 9.5% |
| Sucrose (ground) | 46.1% |
| Low Substituted Hydroxypropyl Cellulose (Binder Liquid) | 7.2% |
| Hydroxypropyl Cellulose | 0.3% |
| Total | 100% |

Example 7

Composition is shown in Table 7. (R)-Lansoprazole (246 g), magnesium carbonate (361 g), sucrose (2,000 g; ground) and low substituted hydroxypropyl cellulose (272 g) were mixed using a vertical granulator to prepare a spraying or dusting material containing an active pharmaceutical ingredient (2,880 g in total). Sucrose-corn starch spherical granules (755.8 g; NONPAREIL 101-750, manufactured by Freund Co.) as cores were put in a centrifugal fluidized bed granulation machine (CF360, manufactured by Freund Co.), and then sprayed or dusted with the spraying or dusting material containing an active pharmaceutical ingredient (2,400 g) while being sprayed with a solution of hydroxypropyl cellulose (2% aqueous solution: W/W) (final spray amount: 8.8 g (solid matter)) to obtain spherical granules. The coating was performed under the conditions of rotor speed: 240 rpm, linear velocity: 271 m/min, and spraying or dusting speed of the active pharmaceutical ingredient per 1 g of the core: 139 mg/min/g. The spherical granules obtained were dried in vacuum at 40° C. for 16 hours, and sieved with a round sieve to obtain active pharmaceutical ingredient granules F with a particle size of 710 μm to 1,400 μm.

TABLE 7

<Composition of Active Pharmaceutical Ingredient Granule (Solid ingredients)>

| (Core) | |
|---|---|
| Sucrose-Starch Spherical Granule (Spraying or Dusting Material Containing Active Pharmaceutical Ingredient) | 23.9% |
| (R)-Lansoprazole | 6.5% |
| Magnesium carbonate | 9.5% |
| Sucrose (ground) | 52.6% |
| Low Substituted Hydroxypropyl Cellulose | 7.2% |

TABLE 7-continued

<Composition of Active Pharmaceutical Ingredient
Granule (Solid ingredients)>

| (Binder Liquid) | |
| --- | --- |
| Hydroxypropyl Cellulose | 0.3% |
| Total | 100% |

Comparative Example 11

Granules of an active pharmaceutical ingredient having the same composition as the active pharmaceutical ingredient granule produced in Example 4 were produced under different production conditions. (R)-Lansoprazole (7,290 g), magnesium carbonate (1,944 g), sucrose (4,800 g, ground) and low substituted hydroxypropyl cellulose (1,458 g) were mixed using a vertical granulator to prepare a spraying or dusting material containing an active pharmaceutical ingredient (15,492 g in total). Sucrose-corn starch spherical granules (4,500 g; NONPAREIL 101-750, manufactured by Freund Co.) as cores were put in a centrifugal fluidized bed granulating machine (CF-600S, manufactured by Freund Co.), and then sprayed or dusted with the spraying or dusting material containing an active pharmaceutical ingredient (14,350 g) while being sprayed with a solution of hydroxypropyl cellulose (2% aqueous solution: W/W) (final spray amount: 43.2 g (solid matter)) to obtain spherical granules. The coating was performed under the conditions of rotor speed: 160 rpm, linear velocity: 339 m/min and spraying or dusting speed of the active pharmaceutical ingredient per 1 g of the core: 78 mg/min/g. The spherical granules obtained were dried in vacuum at 40° C. for 16 hours, and sieved with a round sieve to obtain active pharmaceutical ingredient granules G with a particle size of 710 µm to 1,400 µm.

Example 8

Dissolution profiles of the active pharmaceutical ingredient granules C, D, E and F obtained in Examples 4, 5, 6 and 7 and the active pharmaceutical ingredient granule G obtained in Comparative Example 1 were determined in a phosphate buffer (pH 6.8). As a result, the active pharmaceutical ingredient was almost all dissolved from the active pharmaceutical ingredient granules C, D, E and F in 20 minutes, that is, the dissolution rate was about 100%. On the other hand, the dissolution rate of the active pharmaceutical ingredient from the active pharmaceutical ingredient granule G was about 60% in 20 minutes, that is, the dissolution of the active pharmaceutical ingredient from the active pharmaceutical ingredient granule G was apparently delayed.

Example 9

Composition is shown in Table 8. (R)-Lansoprazole (450 g), magnesium carbonate (330 g), sucrose (1,601 g; ground) and low substituted hydroxypropyl cellulose (248.4 g) were mixed using a vertical granulator to prepare a spraying or dusting material containing an active pharmaceutical ingredient (2,629 g in total). Sucrose-corn starch spherical granules (724.5 g; NONPAREL 101-750, manufactured by Freund Co.) as cores were put in a centrifugal tumbling granulation machine (CF-360, manufactured by Freund Co.), and then sprayed or dusted with the spraying or dusting material containing an active pharmaceutical ingredient (2,416 g) while being sprayed with a solution of hydroxypropyl cellulose (2% aqueous solution: W/W) (final spray amount: 8.4 g (solid matter)) to obtain spherical granules. The coating was performed under the conditions of rotor speed: 240 rpm, linear velocity: 271 m/min and spraying or dusting speed of the active pharmaceutical ingredient per 1 g of the core: 138 mg/min/g. The spherical granules obtained were dried in vacuum at 40° C. for 16 hours, and sieved with a round sieve to obtain active pharmaceutical ingredient granules H with a particle size of 710 µm to 1,400 µm.

The active pharmaceutical ingredient granules H (4,680 g) thus obtained were coated with an intermediate layer coating liquid (6,141 g; solid content: 10%) using a fluidized bed granulation coating machine (MP-10, manufactured by POWREX Co.). The coating was performed under the conditions of air supply rate: 2.4 m$^3$/min, air supply temperature: 70° C. and product temperature: 42° C. (pre-heating temperature, during the process). The spherical granules obtained were dried in vacuum at 40° C. for 16 hours, and sieved with a round sieve to obtain intermediate layer granules C with a particle size of 710 µm to 1,400 µm.

The intermediate layer granules C (4,388 g) thus obtained were put in a fluidized bed granulation coating machine (MP-10, manufactured by POWREX Co.), and then heated at 70° C. for 5 minutes. Subsequently, the granules were coated with a coating liquid (5,875 g, solid content: 183) for forming an enteric coating film. The coating was performed under the conditions of air supply rate: 2.4 m$^3$/min, air supply temperature: 66° C., liquid injection rate: 24 g/min and spray air pressure: 0.3 kg/cm$^2$. The spherical granules thus obtained were dried in vacuum at 40° C. for 16 hours, and sieved with a round sieve to obtain enteric granules B with a particle size from 850 µm to 1,400 µm.

Talc and colloidal silicon dioxide were mixed with the obtained enteric granules B to obtain enteric mixed granules B.

Both of the enteric mixed granules B (80 mg: equivalent to 7.5 mg of (R)-lansoprazole) and the pH-dependent soluble controlled-release mixed granules B obtained in Example 3 (105 mg, equivalent to 22.5 mg of (R)-lansoprazole) were encapsulated into a No. 3 HPMC capsule.

The HPMC capsule thus obtained was dried in vacuum at 40° C. for 2 hours to obtain an HPMC Capsule preparation with a moisture content of 22% RH or less.

TABLE 8

Composition Table

| | Enteric Mixed Granule B |
| --- | --- |
| <Composition of Active Pharmaceutical Ingredient Granule> | |
| Sucrose-Starch Granule | 13.8 mg |
| (Spraying or Dusting Material Containing Active Pharmaceutical Ingredient) | |
| (R)-Lansoprazole | 7.5 mg |
| Magnesium Carbonate | 5.5 mg |
| Sucrose (ground) | 26.68 mg |
| Low Substituted Hydroxypropyl | 4.14 mg |

TABLE 8-continued

Composition Table

| Cellulose (Binder Liquid) | |
|---|---|
| Hydroxypropyl Cellulose | 0.16 mg |
| Purified Water | 7.84 mg |
| Total (Solid matter) | 57.78 mg |

<Composition of Intermediate Layer Coating Liquid>

| | |
|---|---|
| Hydroxypropylmethyl Cellulose | 3.6 mg |
| Talc | 1.44 mg |
| Titanium Oxide | 2.18 mg |
| Purified water | 64.98 mg |
| Total (Solid matter) | 7.22 mg |

<Composition of Intermediate Layer Granule>

| | |
|---|---|
| Active Pharmaceutical Ingredient Granule | 57.78 mg |
| Intermediate Layer Coating Liquid | 7.22 mg |
| Total | 65 mg |

<Composition of Coating Liquid for Enteric Coating Film>

| | |
|---|---|
| Methacrylic Acid Copolymer (Dispersed Liquid) | 32.2 mg (Solid matter 9.66 mg) |
| Polyethyleneglycol 6000 | 0.96 mg |
| Polysorbate 80 | 0.44 mg |
| Titanium Oxide | 0.96 mg |
| Talc | 2.9 mg |
| Purified Water | 45.43 mg |
| Total (Solid matter) | 14.92 mg |

<Composition of Enteric Granule>

| | |
|---|---|
| Intermediate Layer Granule C | 65 mg |
| Coating Liquid for Enteric Coating Film | 14.92 mg |
| Total | 79.92 mg |

<Composition of Enteric Mixed Granule and pH-Dependent Soluble Controlled-Release Mixed Granule>

| | |
|---|---|
| Enteric Mixed Granule B | 79.92 mg |
| pH-Dependent soluble Controlled-Release Granule | — |
| Talc | 0.04 mg |
| Colloidal Silicon Dioxide | 0.04 mg |
| Total | 80.0 mg |

HPMC Capsule Preparation

<Composition of Capsule Preparation (equivalent to 30 mg of (R)-Lansoprazole)>

| | HPMC Capsule Preparation |
|---|---|
| Enteric Mixed Granule B | 80.0 mg |
| pH-Dependent Soluble Controlled-Release Mixed Granule B | 105.0 mg |
| HPMC Capsule | No. 3 Capsule |

Example 10

Both of the enteric mixed granules B (120 mg: equivalent to 11.25 mg of (R)-lansoprzazole) and the pH-dependent soluble controlled-release mixed granules B obtained in Example 3 (157.5 mg: equivalent to 33.75 mg of (R)-lansoprazole were encapsulated into a No 2. HPMC capsule.

The HPMC capsule thus obtained was dried in vacuum at 40° C. for 2 hours to obtain an HPMC Capsule preparation with a moisture content of 22% RH or less.

<Composition of Capsule Preparation (equivalent to 45 mg of (R)-Lansoprazole)>

| | HPMC Capsule Preparation |
|---|---|
| Enteric Mixed Granule B | 120.0 mg |
| pH-Dependent Soluble Controlled-Release Mixed Granule B | 157.5 mg |
| HPMC Capsule | No. 2 Capsule |

Example 11

The enteric mixed granules B (160 mg: equivalent to 15 mg of (R)-lansoprazole) and the pH-dependent soluble controlled-release mixed granules B obtained in Example 3 (210 mg: equivalent to 45 mg of (R)-lansoprazole) were encapsulated into a No. 1 HPMC capsule.

The HPMC capsule thus obtained was dried in vacuum at 40° C. for 2 hours to obtain an HPMC Capsule preparation with a moisture content of 22% RH or less.

<Composition of Capsule Preparation (equivalent to 60 mg of (R)-Lansoprazole)>

| | HPMC Capsule Preparation |
|---|---|
| Enteric Mixed Granule B | 160.0 mg |
| pH-Dependent Soluble Controlled-Release Mixed Granule B | 210.0 mg |
| HPMC Capsule | No. 1 Capsule |

Example 12

Composition is shown in Table 9. (R)-Lansoprazole (225 g), magnesium carbonate (330 g), sucrose (1,826 g: ground) and low substituted hydroxypropyl cellulose (248.4 g) were mixed using a vertical granulator to prepare a spraying or dusting material containing an active pharmaceutical ingredient (2,629 g in total). Sucrose-corn starch spherical granules (724.5 g; NONPAREIL 101-750, manufactured by Freund Co.) as cores were put in a centrifugal tumbling granulation machine (CF-360, manufactured by Freund Co.), and then sprayed or dusted with the spraying or dusting material containing an active pharmaceutical ingredient (2,416 g) while being sprayed with a solution of hydroxypropyl cellulose (2% aqueous solution: W/W) (final spray amount: 8.4 g (solid matter)) to obtain spherical granules. The coating was performed under the conditions of rotor speed: 240 rpm, linear velocity: 271 m/min, and spraying or dusting speed of the active pharmaceutical ingredient per 1 g of the core: 1.38 mg/min/g. The spherical granules obtained were dried in vacuum at 40° C. for 16 hours, and sieved with a round sieve to obtain active pharmaceutical ingredient granules I with a particle size of 710 μm to 1,400 μm.

The active pharmaceutical ingredient granules D (2,311 g) obtained as described above were coated with an intermediate layer coating liquid (3,032 g, solid content: 10%) using a fluidized bed granulation coating machine (MP-10, manufactured by POWREX Co.). The coating was performed under the conditions of air supply rate: 1.5 m³/min, air supply temperature: 70° C. and product temperature: 42° C. (pre-heating temperature, during the process). The spherical granules thus obtained were dried in vacuum at 40° C. for 16 hours, and sieved with a round sieve to obtain intermediate layer granules 0 with a particle size of 710 μm to 1,400 μm.

The intermediate layer granules D (2,145 g) obtained as described above were put in a fluidized bed granulation coating machine (MP-10, manufactured by POWREX Co.), and then heated at 70° C. for 5 minutes. Subsequently, the granules were coated with a coating liquid (2,872 g, solid content: 18%) for an enteric coating film. The coating was performed under the conditions of air supply rate: 1.5 m³/min, air supply temperature: 70° C., liquid injection rate: 16.5 g/min and spray air pressure: 3 kg/cm². The spherical granules thus obtained were dried in vacuum at 40° C. for 16 hours, and sieved with a round sieve to obtain enteric granules C with a particle size of 850 μm to 1,400 μm.

The enteric granules C thus obtained was mixed with talc and light silicic acid anhydride to obtain enteric mixed granules C.

Both of the enteric mixed granules C (80 mg, equivalent to 7.5 mg of (R)-lansoprazole) and the pH-dependent soluble controlled-release mixed granules B obtained in Example 3 (52.5 mg, equivalent to 22.5 mg of (R)-lansoprazole) were encapsulated into a No. 4 HPMC capsule.

The HPMC capsule thus obtained was dried in vacuum at 40° C. for 2 hours to obtain an HPMC Capsule preparation with a moisture content of 22% RH or less.

TABLE 9

| Composition Table | |
|---|---|
| | Enteric Mixed Granule C |
| <Composition of Active Pharmaceutical Ingredient Granule> | |
| Sucrose-Starch Spherical Granule (Spraying or Dusting Material Containing Active Pharmaceutical Ingredient) | 13.8 mg |
| (R)-Lansoprazole | 3.75 mg |
| Magnesium Carbonate | 5.5 mg |
| Sucrose (ground) | 30.43 mg |
| Low Substituted Hydroxypropyl Cellulose | 4.14 mg |
| (Binder Liquid) | |
| Hydroxypropyl Cellulose | 0.16 mg |
| Purified Water | 7.84 mg |
| Total (solid matter) | 57.78 mg |
| <Composition of Intermediate Layer Coating Liquid> | |
| Hydroxypropylmethyl Cellulose | 3.6 mg |
| Talc | 1.44 mg |
| Titanium Oxide | 21.8 mg |
| Purified Water | 64.98 mg |
| Total (Solid matter) | 7.22 mg |
| <Composition of Intermediate Layer Granule> | |
| Active Pharmaceutical Ingredient Granule I | 57.78 mg |
| Intermediate Layer Coating liquid | 7.22 mg |
| Total | 65 mg |
| <Composition of Coating Liquid for Enteric Coating Film> | |
| Methacrylic Acid Copolymer (Dispersion Liquid) | 32.2 mg (Solid matter 9.66 mg) |
| Polyethyleneglycol 6000 | 0.96 mg |
| Polysorbate 80 | 0.44 mg |
| Titanium Oxide | 0.96 mg |
| Talc | 2.9 mg |
| Purified Water | 45.43 mg |
| Total (Solid matter) | 14.92 mg |

TABLE 9-continued

| Composition Table | |
|---|---|
| <Composition of Enteric Granule> | |
| Intermediate Layer Granule D | 65 mg |
| Coating Liquid for Enteric Coating Film | 14.92 mg |
| Total | 79.92 mg |
| <Composition of Enteric Mixed Granule and pH-Dependent Soluble Controlled-Release Mixed Granule> | |
| Enteric Granule C | 79.92 mg |
| pH-Dependent Soluble Controlled-Release Granule | — |
| Talc | 0.04 mg |
| Light Silicic Acid Anhydride | 0.04 mg |
| Total | 80.0 mg |

| | HPMC Capsule Preparation |
|---|---|
| <Composition of Capsule Preparation (equivalent to 1.5 mg of (R)-Lansoprazole)> | |
| Enteric Mixed Granule C | 80.0 mg |
| pH-Dependent Soluble Controlled-Release Mixed Granule B | 52.5 mg |
| HPMC Capsule | No. 4 Capsule |

Example 13

Both of the enteric mixed granule A (58 mg; equivalent to 15 mg of (R)-lansoprazole) and the pH-dependent soluble controlled-release mixed granule B (210 mg; equivalent to 45 mg of (R)-lansoprazole) which were obtained in Example 3 were encapsulated into a No. 2 HPMC capsule.

The HPMC capsule thus obtained was dried in vacuum at 40° C. for 2 hours to obtain an HPMC Capsule preparation with a moisture content of 22% RH or less.

| <Composition of Capsule Preparation> | |
|---|---|
| | EPMC Capsule preparation |
| Enteric Mixed Granule A | 58.0 mg |
| pH-Dependent Soluble Controlled-Release Mixed Granule B | 210.0 mg |
| HPMC Capsule | No. 2 Capsule |

INDUSTRIAL APPLICABILITY

According to the method for producing granules and the method for improving variation in the dissolution of a biologically active substance of the present invention, in a process for producing granules containing a biologically active substance, simply heating the temperature of granules to a predetermined temperature and then maintaining the granules at the said temperature for a predetermined time can lead to reduced variation in the dissolution profile of the biologically active substance, and thereby a design of a pharmaceutical preparation capable of stably maintaining an effective blood concentration of a drug is facilitated.

The invention claimed is:
1. A centrifugal fluidized bed granulation method for granules of an active pharmaceutical ingredient, which comprises spraying or dusting a spraying or dusting material containing an active pharmaceutical ingredient containing a biologically active substance at a spraying or dusting speed of about 90 mg/min or more per 1 g of cores while spraying a binder liquid to cores, wherein a total feeding weight per unit area for a centrifugal fluidized bed coating granulation machine is about 1.5 g/cm$^2$ or more.

2. The method according to claim 1, wherein the spraying or dusting speed of the spraying or dusting material containing an active pharmaceutical ingredient is from about 90 to about 250 mg/min.

3. The method according to claim 1, wherein the ratio of (spraying or dusting speed of the spraying or dusting material containing an active pharmaceutical ingredient per 1 g of cores)/(linear velocity) is from 0.27 to 2.

4. The method according to claim 1, wherein the total feeding weight per unit area for a centrifugal fluidized bed coating granulation machine is from about 1.5 to about 6 g/cm$^2$.

5. A granule obtained by the granulation method according to claim 1.

* * * * *